(12) United States Patent
Miyamoto et al.

(10) Patent No.: US 10,677,791 B2
(45) Date of Patent: Jun. 9, 2020

(54) FLUIDIC DEVICE, FLUID CONTROL METHOD, TESTING DEVICE, TESTING METHOD, AND FLUIDIC DEVICE MANUFACTURING METHOD

(71) Applicant: NIKON CORPORATION, Minato-ku, Tokyo (JP)

(72) Inventors: Kenji Miyamoto, Yokohama (JP); Masaru Kato, Saitama (JP)

(73) Assignee: NIKON CORPORATION, Tokyo (JP)

( * ) Notice: Subject to any disclaimer, the term of this patent is extended or adjusted under 35 U.S.C. 154(b) by 393 days.

(21) Appl. No.: 15/386,224

(22) Filed: Dec. 21, 2016

(65) Prior Publication Data

US 2017/0102383 A1 Apr. 13, 2017

Related U.S. Application Data

(63) Continuation of application No. PCT/JP2015/069018, filed on Jul. 1, 2015.

(30) Foreign Application Priority Data

Jul. 1, 2014 (JP) ................................. 2014-136294

(51) Int. Cl.
- *B01L 3/00* (2006.01)
- *G01N 33/543* (2006.01)
- *F16K 99/00* (2006.01)

(52) U.S. Cl.
CPC .. *G01N 33/54386* (2013.01); *B01L 3/502723* (2013.01); *B01L 3/502738* (2013.01);
(Continued)

(58) Field of Classification Search
CPC ........ G01N 33/54386; G01N 33/54366; F16K 99/0028; F16K 99/0059; F16K 99/0015;
(Continued)

(56) References Cited

U.S. PATENT DOCUMENTS

| | | | |
|---|---|---|---|
| 6,007,046 A | * | 12/1999 | Rothermel ................ F15C 3/04 137/606 |
| 6,296,020 B1 | | 10/2001 | McNeely et al. |
| 2010/0303687 A1 | * | 12/2010 | Blaga .................. B01L 3/50273 422/504 |
| 2013/0032235 A1 | | 2/2013 | Johnstone et al. |
| 2014/0079571 A1 | | 3/2014 | Hui et al. |

FOREIGN PATENT DOCUMENTS

| | | |
|---|---|---|
| JP | A 2002-527250 | 8/2002 |
| WO | WO 2000/022436 | 4/2000 |

OTHER PUBLICATIONS

International Search Report for International Application No. PCT/JP/2015/069018 dated Oct. 6, 2015, with translation; 8 pages.

(Continued)

*Primary Examiner* — Rebecca L Martinez
(74) *Attorney, Agent, or Firm* — Squire Patton Boggs (US) LLP

(57) ABSTRACT

A fluidic device includes a valve configured to adjust a fluid flow in a first direction of a flow path. The fluidic device includes: a diaphragm of the valve; a first substrate having a groove that constitutes the flow path and a protrusion part at a position facing the diaphragm in the groove; and a second substrate to which the diaphragm is fixed at a first fixation part and a second fixation part, wherein a length from a first end part of the protrusion part to a second end part of the protrusion part seen in the first direction is greater than a length from the first fixation part to the second fixation part.

18 Claims, 10 Drawing Sheets

(52) U.S. Cl.
CPC ...... *F16K 99/0015* (2013.01); *F16K 99/0028* (2013.01); *F16K 99/0059* (2013.01); *B01L 2200/0689* (2013.01); *B01L 2300/0636* (2013.01); *B01L 2300/0816* (2013.01); *B01L 2300/0864* (2013.01); *B01L 2300/0867* (2013.01); *B01L 2400/0655* (2013.01); *B01L 2400/0688* (2013.01); *F16K 2099/008* (2013.01); *F16K 2099/0073* (2013.01); *G01N 33/54366* (2013.01)

(58) Field of Classification Search
CPC ....... F16K 2099/0073; F16K 2099/008; B01L 2300/0864; B01L 3/502738; B01L 3/502723; B01L 2400/0655; B01L 2300/0867; B01L 2200/0689; B01L 2300/0636; B01L 2300/0816; B01L 2400/0688
See application file for complete search history.

(56) References Cited

OTHER PUBLICATIONS

Jiang, C. et al. "Implementation of the shape-memory polymer microfluidic valve to plastic-based microfluidic devices," JSAP Spring Meeting Koen Yokoshu, Mar. 3, 2014, Dai 61 Kai, pp. 12-434, presentation No. 17p-E14-12.

Written Opinion for International Application No. PCT/JP/2015/069018 dated Oct. 6, 2015, with translation; 18 pages.

Zhang, W. et al., "PMMA/PDMS valves and pumps for disposable microfluidics," Lab Chip, Nov. 7, 2009, vol. 9, pp. 3088-3094.

Notice of Reasons for Rejection issued by the Japanese Patent Office dated Apr. 2, 2019 for Japanese Patent Application No. 2016-531423, with English translation, 9 pages.

\* cited by examiner

FLUIDIC DEVICE, FLUID CONTROL METHOD, TESTING DEVICE, TESTING METHOD, AND FLUIDIC DEVICE MANUFACTURING METHOD

CROSS-REFERENCE TO RELATED APPLICATION

This is a Continuation Application of International Application No. PCT/JP2015/069018 filed on Jul. 1, 2015, which claims priority on Japanese Patent Application No. 2014-136294 filed on Jul. 1, 2014. The contents of the aforementioned applications are incorporated herein by reference.

BACKGROUND

Field of the Invention

The present invention relates to a fluidic device, a fluid control method, a testing device, a testing method, and a fluidic device manufacturing method.

Background

In the related art, as a fluidic device including a valve that controls a fluid flow in a flow path formed at a bond surface between a first substrate and a second substrate that constitute a laminate substrate, a fluidic device including a valve having a three-layer structure in which a resin sheet is sandwiched at the interface of the first substrate and the second substrate is known ("PMMA/PDMS Valves and Pumps for Disposable Microfluidics." Lab Chip. 2009 Nov. 7; 9 (21): 3088-94, Zhang W et al.).

SUMMARY

A problem to be solved of an aspect of the invention is to provide a fluidic device capable of easily controlling a fluid flow in a flow path, a fluid control method using the fluidic device, a testing device using the fluidic device, a testing method using the testing device, and a manufacturing method of the fluidic device.

(1) An aspect of the present invention is a fluidic device including a valve configured to adjust a fluid flow in a first direction of a flow path, the fluidic device including: a diaphragm of the valve; a first substrate having a groove that constitutes the flow path and a protrusion part at a position facing the diaphragm in the groove; and a second substrate to which the diaphragm is fixed at a first fixation part and a second fixation part, wherein a length from a first end part of the protrusion part to a second end part of the protrusion part seen in the first direction is greater than a length from the first fixation part to the second fixation part.

(2) An aspect of the present invention is a fluid control method in a fluidic device, the fluidic device including: a diaphragm of a valve; a first substrate having a groove that constitutes a flow path and a protrusion part at a position facing the diaphragm of the groove; and a second substrate to which the diaphragm is fixed at a first fixation part and a second fixation part, wherein a length from a first end part of the protrusion part to a second end part of the protrusion part seen in a first direction of the flow path is greater than a length from the first fixation part to the second fixation part, wherein the control method includes: (a) deforming the diaphragm and pressing the diaphragm to the protrusion part; (b) introducing a fluid including a gas and a liquid to the flow path constituted by the groove and delivering the fluid until a front end of the liquid arrives before the protrusion part; (c) by reducing a deformation amount of the diaphragm to thereby reduce an added pressure to the protrusion part according to the diaphragm, stopping the front end of the liquid by the protrusion part and allowing only a gas that is present between the protrusion part and the front end of the liquid to pass; and (d) by further reducing or releasing the deformation amount of the diaphragm, allowing the liquid that has been stopped by the protrusion part to pass.

(3) A fluidic device according to an aspect of the present invention includes a branch route in which a first flow path, a second flow path, and a third flow path are connected to each other at a single branch point, wherein the second flow path includes at least one valve configured to adjust a fluid flow in a flow path, and the third flow path has a first protrusion part in the vicinity of the branch point.

(4) A fluid control method according to an aspect of the present invention is a method of controlling a fluid in the fluidic device of (3) described above, the method including: (a) by making an inside of the second flow path to be in a negative pressure to thereby introduce a first liquid from a first end part of the first flow path, allowing the first liquid to pass through the branch point to be delivered to the second flow path and preventing the first liquid from flowing into the third flow path from the branch point according to a flow path resistance of a first protrusion part provided on the third flow path; (b) after (a), allowing the first liquid that is present in the first flow path and the branch point to fully flow into the second flow path; and (c) after (b), by making an inside of the third flow path to be in a negative pressure to thereby introduce a second liquid from the first flow path, allowing the second liquid to pass through the branch point to be delivered to the third flow path.

(5) An aspect of the present invention is a fluidic device including a branch route in which a first flow path, a second flow path, and a third flow path are connected to each other at a single branch point, wherein the second flow path includes at least one valve configured to adjust a fluid flow in a flow path, and the second flow path has, in the vicinity of the branch point, a liquid reservoir part and a protrusion part in this order.

(6) A fluid control method according to an aspect of the present invention is a method of controlling a fluid in the fluidic device of (5) described above, the method including: (a) by introducing a first liquid from a first end part of the first flow path, allowing the first liquid to pass through the branch point to be delivered to the third flow path, and by allowing part of the first liquid to enter the liquid reservoir part in the second flow path from the branch point, stopping the entering before the protrusion part; (b) after (a), allowing the first liquid that is present in the first flow path and the branch point to fully flow into the third flow path; and (c) after (b), recovering the part of the first liquid that has been stopped at the liquid reservoir part.

(7) A fluidic device according to an aspect of the present invention includes a first substrate in which a groove that constitutes a first flow path, a second flow path, a third flow path, a fourth flow path, and a fifth flow path is formed on a first surface; an elastomer sheet that covers the first surface; and a second substrate having a second surface that is bonded via the elastomer sheet to the first surface, wherein the groove formed on the first substrate constitutes a route in which: a first end part of the first flow path communicates outside; a second end part of the first flow path, a first end part of the second flow path, a first end part of the third flow path, and a first end part of the fourth flow path are connected to each other at a single branch point; a second end part of the second flow path, a second end part of the third flow path, a second end part of the fourth flow path, and a first end part of the fifth flow path are connected to each other at a single merging point; and a second end part of the fifth flow path communicates outside, at least one first protrusion part that shallows a depth of the groove is formed in the vicinity of the branch point of the groove that constitutes the second flow path, and at least one second protrusion part that shallows a depth of the groove is formed in the vicinity of the branch point of the groove that constitutes the third flow path, whereby a flow path resistance at the branch point is large in the order of the fourth flow path, the third flow path, and the second flow path.

(8) A testing device according to an aspect of the present invention is a testing device configured to inspect an inspection target material included in a liquid sample using the fluidic device of (7) described above, wherein a capture part to which a capture material that can be coupled to the inspection target material is fixed is provided at the groove that constitutes the fifth flow path, a first supply part including a detection material that can be coupled to a complex of the inspection target material and the capture material is provided at the groove that constitutes the third flow path, and a second supply part including a signal material configured to emit a signal by which it can be detected that the detection material is present at the capture part is provided at the groove that constitutes the second flow path.

(9) A testing method according to an aspect of the present invention is a method of inspecting an inspection target material included in a liquid sample using the testing device of (8) described above, the method including: introducing the liquid sample from the first end part of the first flow path to arrive at the branch point; introducing the liquid sample to the fourth flow path having the smallest flow path resistance among the second flow path, the third flow path, and the fourth flow path to arrive at the merging point; and introducing the liquid sample to the fifth flow path connected to the merging point, whereby the inspection target material included in the liquid sample is coupled to the capture material at the capture part.

(10) An aspect of the present invention is a manufacturing method of a fluidic device including a valve configured to adjust a fluid flow in a flow path, the method including: (a) preparing a first resin substrate in which a groove that has a first depth and that can function as a flow path is formed on at least one surface and a protrusion part is formed such that a depth of the flow path is a second depth that is smaller than the first depth at part of a bottom surface of the groove, a second resin substrate in which a base structure that constitutes the valve is formed on a second surface, and a thinned elastomer sheet; (b) overlapping the first resin substrate, the elastomer sheet, and the second resin substrate such that the elastomer sheet is sandwiched between a first surface of the first resin substrate and the second surface of the second resin substrate and such that the protrusion part faces the base structure; and (c) obtaining a substrate bond body by thermocompression bonding of the first resin substrate, the elastomer sheet, and the second resin substrate.

DESCRIPTION OF EMBODIMENTS

<<Fluidic Device>>

Figure 1:
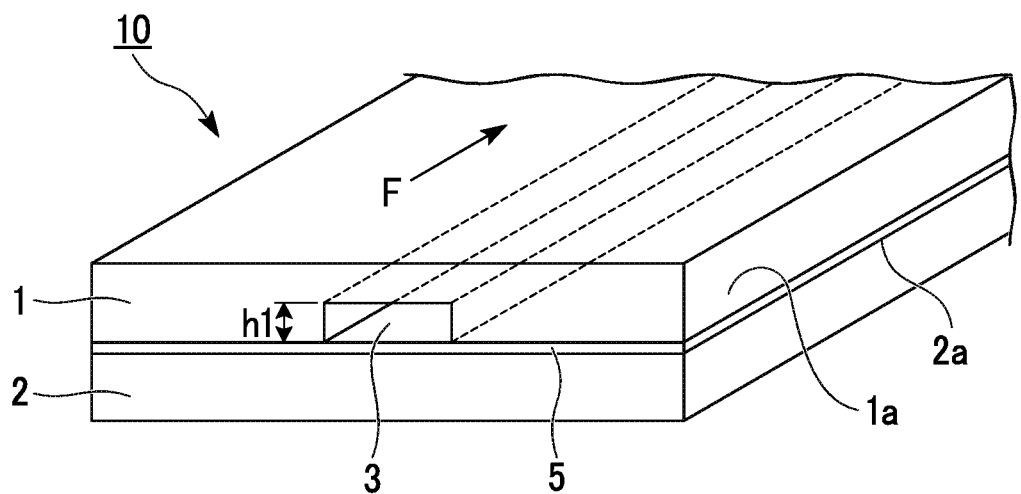
FIG. 1 is a perspective view showing a side surface of a fluidic device.
Figure 2:
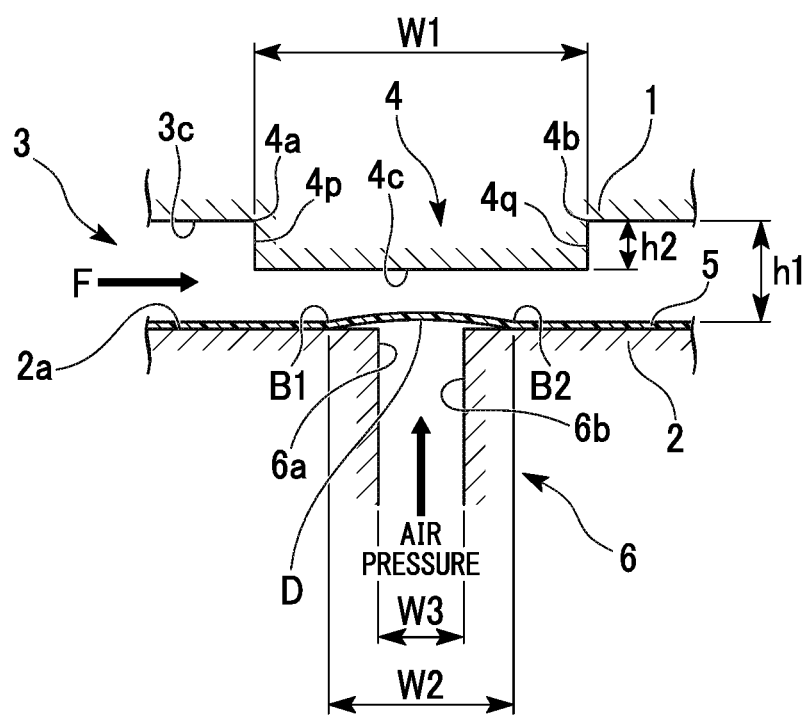
FIG. 2 is an example of a cross-sectional view in a thickness direction of a first substrate and a second substrate that constitute the fluidic device.

As shown in FIG. 1 and FIG. 2, a first embodiment of a fluidic device according to the present invention is a fluidic device 10 including a valve that adjusts a fluid flow in a first direction F in a flow path 3.

The fluidic device 10 is a fluidic device including a valve that adjusts a fluid flow in the first direction F of the flow path 3. The fluidic device 10 includes: a diaphragm D of the valve, a first substrate 1 having a groove 3 that constitutes the flow path 3 and a protrusion part 4 at a position facing the diaphragm D in the groove 3; and a second substrate 2 to which the diaphragm D is fixed at a first fixation part B1 and a second fixation part B2, and a length W1 from a first end part B1 of the protrusion part 4 to a second end part B2 of the protrusion part 4 seen in the first direction F is greater than a length W2 from the first fixation part B1 to the second fixation part B2. The first direction F of the flow path 3 is a direction along an extension direction of the groove 3 that constitutes the flow path 3.

The fluidic device 10 includes: the first substrate 1 having the groove 3 that constitutes the flow path 3 and the protrusion part 4 at a bottom surface $3c$ (a wall surface $3c$ of the flow path 3) of the groove 3; the diaphragm D of the valve arranged at a position facing the protrusion part 4; and the second substrate to which the diaphragm D is fixed at the first fixation part B1 and the second fixation part B2. The length W1 from a first end part $4a$ of the protrusion part 4 to a second end part $4b$ of the protrusion part 4 seen in the extension direction F of the flow path 3 is greater than the length W2 from the first fixation part B1 to the second fixation part B2. The fluidic device 10 is a diaphragm valve.

The fluidic device 10 includes: the first substrate 1 in which the groove 3 having a depth h1 that constitutes the flow path 3 is formed on a first surface $1a$; the second substrate 2 in which a base structure 6 that constitutes the valve for controlling a flow volume, a flow rate, or a flow of the fluid in the flow path 3 is formed on a second surface $2a$; and a sheet 5 that constitutes the diaphragm D of the valve and is sandwiched between the first surface $1a$ of the first substrate 1 and the second surface $2a$ of the second substrate 2.

The base structure 6 is a structure body that constitutes the valve and that is provided on the second substrate 2 which causes at least part of the sheet 5 to function as the diaphragm D. Examples of the base structure 6 include a through-hole or a non-through-hole provided on the second surface $2a$.

In the fluidic device 10, the protrusion part 4 having a height h2 is formed at a position facing the diaphragm D and the base structure 6 in the groove 3. The depth of the groove 3 is h1-h2 at the position facing the diaphragm D and the base structure 6 in the groove 3, and the length W1 from the first end part $4a$ of the protrusion part 4 to the second end part $4b$ of the protrusion part 4 seen in the extension direction F of the groove 3 is greater (longer) than a length W3 of the base structure 6 seen in the extension direction F of the groove 3.

The protrusion part 4 is arranged at the groove 3 and is a structure body (convex part, step part) that narrows the flow path height. The first end part $4a$ of the protrusion part 4 is an end part positioned on the most upstream side of the flow path 3 in the protrusion part 4. For example, as shown in FIG. 2 to FIG. 6, when an angle θ1 formed of a side surface $4p$ facing the upstream side of the protrusion part 4 and the bottom surface $3c$ of the groove 3 is 90° or less, the first end part $4a$ means a part at which the bottom surface $3c$ of the groove 3 and the bottom of the side surface $4p$ of the protrusion part 4 cross.

The second end part $4b$ of the protrusion part 4 is an end part positioned on the most downstream side of the flow path 3 in the protrusion part 4.

Figure 5:
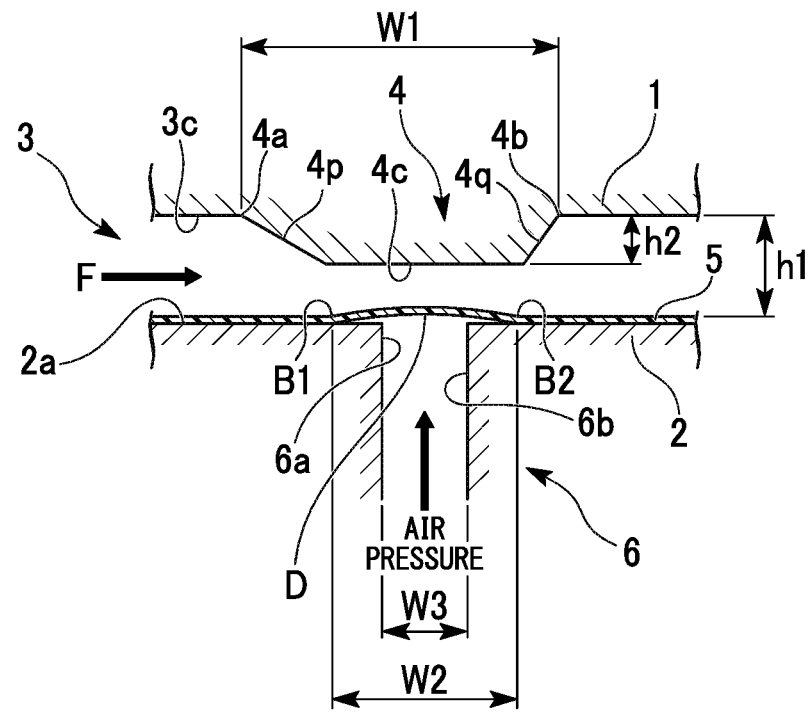
FIG. 5 is an example of a cross-sectional view in the thickness direction of the first substrate and the second substrate that constitute the fluidic device.

For example, as shown in FIG. 5, when an angle θ2 formed of a side surface $4q$ facing the downstream side of the protrusion part 4 and the bottom surface $3c$ of the groove 3 is 90° or less, the second end part $4b$ means a part at which the bottom surface $3c$ of the groove 3 and the bottom of the side surface $4q$ of the protrusion part 4 cross.

The side surfaces $4p$, $4q$ of the protrusion part 4 are non-parallel planes to the bottom surface $3c$ of the groove 3. The protrusion part 4 may include a top surface $4c$ that is substantially parallel to the bottom surface $3c$ of the groove 3. The top surface $4c$ is arranged so as to easily come into contact with the diaphragm D. The protrusion part 4 is arranged at a position of the groove that faces a part at which the sheet deforms to function as the diaphragm of the valve.

When a fluid is caused to flow along the extension direction F of the flow path 3, the depth of the groove 3 shallows at the valve structure including the sheet 5, the protrusion part 4, and the base structure 6. For example, since the depth of the groove 3 on a more upstream side than the protrusion part 4 is h1, and the height (thickness) of the protrusion part is h2, the depth of the groove 3 positioned between the protrusion part 4 and the base structure 6 is h1-h2. In this way, the groove 3 shallows immediately below the protrusion part 4, and therefore, a flow path resistance when liquid flows from the first end part $4a$ on the upstream side of the protrusion part 4 to the second end part $4b$ on the downstream side of the protrusion part 4 increases. Since the protrusion part 4 has a sufficient length W1, a sufficient flow path resistance can be obtained. As a result, it is possible to easily stop the flow of the fluid.

Examples of methods for controlling a fluid flow include a control method that strengthen and weaken the pressure of delivering a fluid or a control method according to opening and closing of a valve.

The sheet 5 is closely attached to the first surface $1a$ of the first substrate 1 and covers the groove 3 to thereby constitute a bottom part (wall surface) of the flow path 3. In a region in contact with the base structure 6, the sheet 5 constitutes the bottom part of the flow path 3 when the valve is in an "open state", and part of the sheet 5 falls inside the groove 3 when the valve is in a "closed state" (refer to FIG. 3 to FIG. 4). Accordingly, in the open state, the liquid introduced to the flow path 3 can pass through a valve structure (valve) including the protrusion part 4 and the base structure 6. On the other hand, in the closed state, the sheet 5 immediately above the base structure 6 falls (expands) toward the protrusion part 4 to close the groove 3, and therefore, the liquid does not easily pass through the protrusion part 4. Part of the sheet 5 that falls may come into contact with the protrusion part 4 or may not come into contact with the protrusion part 4. When the sheet 5 falls until the sheet 5 comes into contact with the protrusion part 4, the flow of the liquid can be further reliably stopped. The material of the sheet 5 may be, for example, an elastomer or may be a non-elastomer.

Figure 3:
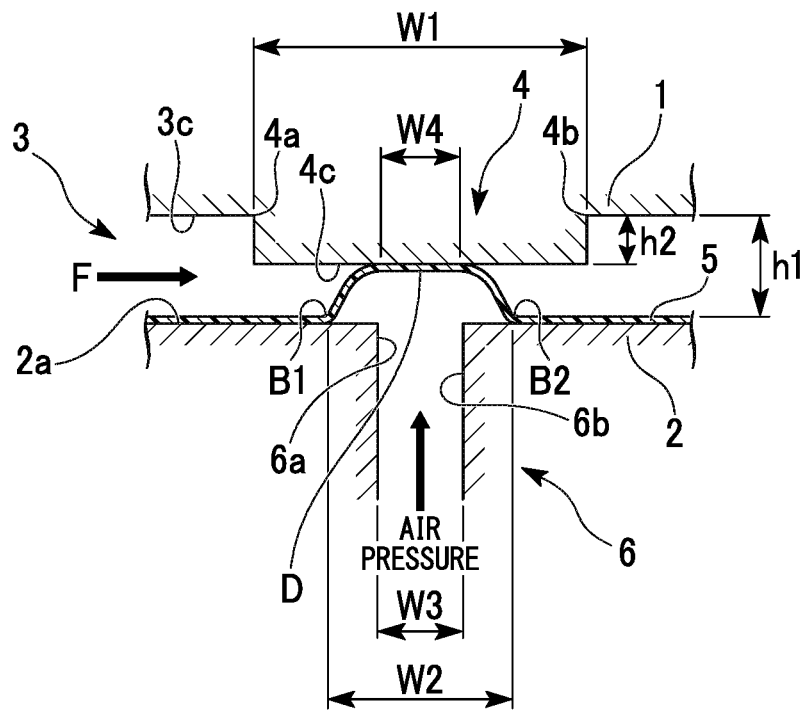
FIG. 3 is an example of a cross-sectional view in the thickness direction of the first substrate and the second substrate that constitute the fluidic device.
Figure 4:
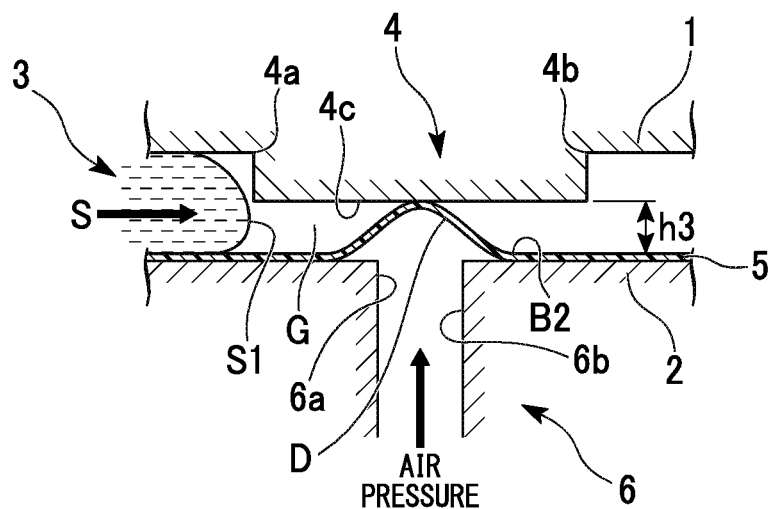
FIG. 4 is an example of a cross-sectional view in the thickness direction of the first substrate and the second substrate that constitute the fluidic device.

In the closed state of the valve, the top surface $4c$ of the protrusion part 4 and the diaphragm D can be in contact with each other (refer to FIG. 3 to FIG. 4). Further, the diaphragm D can be pressed to the top surface $4c$ of the protrusion part 4. For example, when the sheet 5 is an elastomer, the deformed diaphragm D is easily attached closely to the protrusion part 4. In the closed state of the valve, when the cross-section in the thickness direction of the first substrate 1 and the second substrate 2 is seen, a length W4 along the flow path 3 of an area where the top surface 4c of the protrusion part 4 and the diaphragm D are in contact with each other is shorter than the length W1 along the flow path of the protrusion part 4 (refer to FIG. 3).

In the fluidic device 10, when seen in the thickness direction (a direction in which the first substrate 1 and the second substrate 2 are overlapped) of the second substrate 2, the sheet 5 and the second surface 2a are fixed to each other at least at the first fixation part B1 and the second fixation part B2 to bridge the base structure 6. The length W2 from the first fixation part B1 to the second fixation part B2 when seen in the extension direction F of the groove 3 is smaller (shorter) than the length W1 of the protrusion part 4 and is equal to or more than the length W3 of the base structure 6 or is greater (longer) than the length W3.

As described above, when there is a relationship in which "the length W2 from the first fixation part B1 to the second fixation part B2≥the length W3 of the base structure 6 (the length W2 is longer than or the same as the length W3)", in the closed state of the valve, part of the sheet 5 sufficiently falls inside the groove 3 and can easily come into contact with the protrusion part 4.

As a result, the flow of the liquid in the flow path can be easily stopped. Further, when there is a relationship in which "the length W2 from the first fixation part B1 to the second fixation part B2>the length W3 of the base structure 6 (the length W2 is longer than the length W3)", in the closed state of the valve, part of the sheet 5 further easily falls inside the groove 3 and comes into contact with the protrusion part 4. As a result, the flow of the liquid in the flow path can be further easily stopped.

As described above, when there is a relationship in which "the length W1 of the protrusion part 4>the length W2 from the first fixation part B1 to the second fixation part B2 (the length W1 is longer than the length W2)", the response of the sheet 5 is improved in switching between the open and closed states of the valve. In comparison with a case where there is a relationship (relationship opposite to the above-described relationship) in which "the length W1 of the protrusion part 4<the length W2 from the first fixation part B1 to the second fixation part B2 (the length W1 is shorter than the length W2)", a required time and the deformation of the sheet 5 until the sheet 5 falls inside the groove 3 and comes into contact with the protrusion part 4 is smaller.

The length (length of the protrusion part 4 along the width direction of the flow path 3) of the protrusion part 4 in a direction perpendicular to the extension direction of the groove 3 is not particularly limited and may be the same as the length in the width direction of the groove 3 or may be shorter than the length in the width direction of the groove 3.

Figure 6:
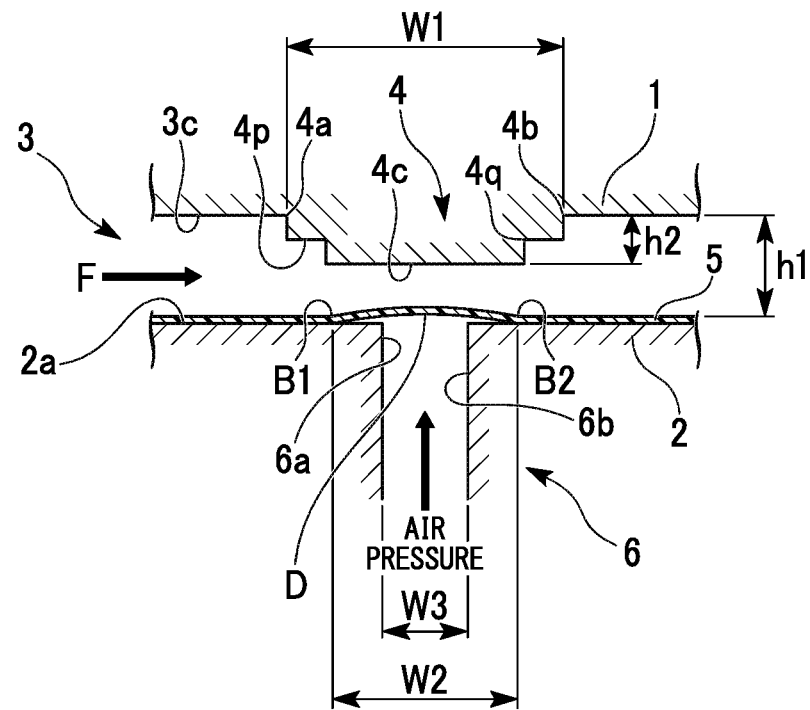
FIG. 6 is an example of a cross-sectional view in the thickness direction of the first substrate and the second substrate that constitute the fluidic device.

The side surface 4p including the first end part 4a of the protrusion part 4 is a plane that faces the fluid that flows in at the upstream side of the flow path 3. In the cross-section in the thickness direction of the first substrate 1, the profile line of the side surface 4p may be any of a straight line and a curved line. The side surface 4p may be a flat plate plane or may be a curved plane. The angle θ1 formed of the side surface 4p and the bottom surface 3c of the groove 3 may be any of an acute angle, a right angle, and an obtuse angle and may be, for example, in the range of 30 to 150 degrees. The formed angle θ1 in the example of FIG. 2 is 90 degrees, and the formed angle θ1 in the example of FIG. 5 is 30 degrees. The side surface 4p may include one or more steps as shown in FIG. 6.

The side surface 4q including the second end part 4b of the protrusion part 4 is a plane that sees off the fluid that passes through the protrusion part 4 at the downstream side of the flow path 3. That is, the side surface 4q is a plane directed in a direction (first direction F) in which the fluid flows. In the cross-section in the thickness direction of the first substrate 1, the profile line of the side surface 4q may be any of a straight line and a curved line. The angle θ2 formed of the side surface 4q and the bottom surface 3c of the groove 3 may be any of an acute angle, a right angle, and an obtuse angle and may be, for example, in the range of 30 to 150 degrees. The formed angle θ2 in the example of FIG. 2 is 90 degrees, and the formed angle θ2 in the example of FIG. 5 is 60 degrees. The side surface 4q may include one or more steps as shown in FIG. 6.

Figure 7:
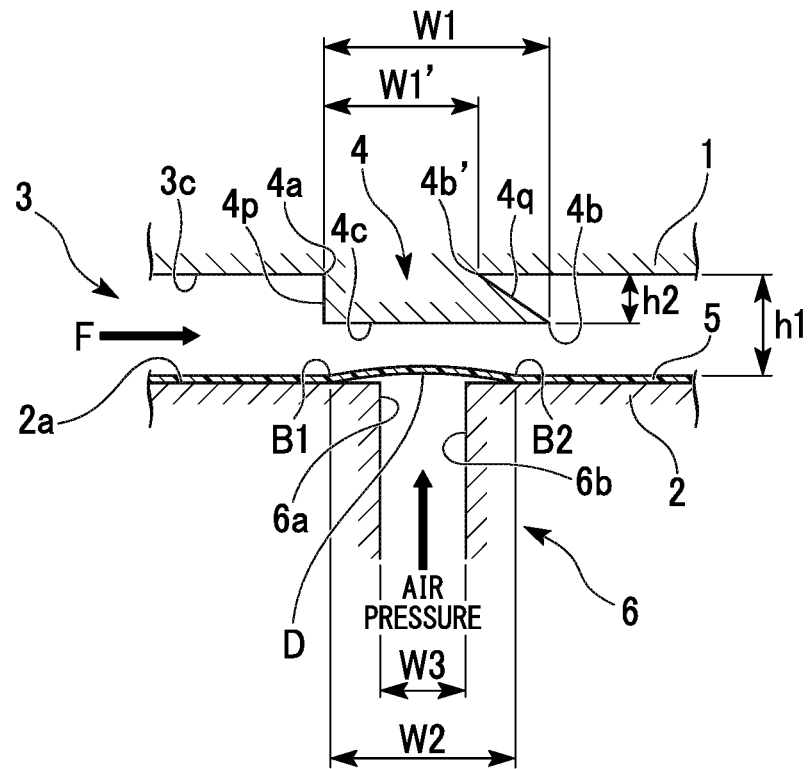
FIG. 7 is an example of a cross-sectional view in the thickness direction of the first substrate and the second substrate that constitute the fluidic device.

In the example of FIG. 7, the angle θ2 formed of the side surface 4q including the second end part 4b of the protrusion part 4 and the bottom surface 3c of the groove 3 is an obtuse angle and is about 150 degrees. When the formed angle θ2 is an obtuse angle, the second end part 4b that defines the length W1 along the extension direction F of the groove 3 of the protrusion part 4 is an end when the protrusion part 4 is projected onto the bottom surface 3c of the groove 3, and in the example of FIG. 7, the end on the downstream side of the top surface 4c is the second end part 4b of the protrusion part 4.

In the fluidic device 10, as the base structure 6, inner side surfaces 6a, 6b that constitute a hole 6 having an opening part that opens facing the groove 3 are provided in the thickness direction of the second substrate 2. The hole 6 may be a through-hole or may be a non-through-hole. A region which is not shown in the drawing of the hole 6 may be extended in the thickness direction of the second substrate 2 or may be extended in a direction other than the thickness direction of the second substrate 2. The thickness direction of the second substrate 2 may be a direction substantially perpendicular to the second surface 2a or may form a slant of, for example, about 45 degrees with respect to the second surface 2a.

In the fluidic device 10, when seen in the extension direction of the groove 3, the length W3 of the base structure 6 described above is the length of bridging between edges that constitute the opening part of the hole 6. Generally, the length W3 corresponds to the diameter of the opening part of the hole 6. When the opening part is seen in the thickness direction of the second substrate 2, the shape of the opening part is not particularly limited. Examples of the shape include a rectangle, a square, other polygons, a circle, and an ellipse. The length of the opening part along the width direction of the groove 3 may be the same as the length in the width direction of the groove 3, may be longer than the length in the width direction of the groove 3, or may be shorter than the length in the width direction of the groove 3. The center of the opening part is positioned, for example, at the center part in the width direction of the groove 3.

As shown in FIG. 3 and FIG. 4, by increasing the pressure of the inside of the hole 6, it is possible to cause the sheet 5 to fall (expand) inside the groove 3, and the flow path 3 can be closed. As an example, when the hole 6 is a through-hole, by delivering a fluid such as air or water into the through-hole from an end part (not shown) on the opposite side of an end part that constitutes the opening part, it is possible to expand the sheet 5 according to a fluid pressure such as air pressure or water pressure. As another example, when the hole 6 is a non-through-hole, by heating air in the non-through-hole to expand the air, it is possible to expand the sheet 5.

In the fluidic device 10, the material of the sheet 5 is not particularly limited as long as the sheet 5 can form the diaphragm D of the valve, and examples of the sheet 5 include a resin sheet and an elastomer sheet. The thickness of the sheet 5 is not particularly limited as long as the sheet 5 can form the diaphragm D of the valve, and examples of the thickness include 100 μm to 1000 μm. When the sheet 5 is an elastomer sheet, the thickness of the elastomer sheet 5 is, for example, 300 μm to 800 μm.

The material that constitutes the first substrate 1 and the second substrate 2 is not particularly limited, and examples of the material include a known material such as resin, glass, semiconductor, metal, and ceramics.

In the fluidic device 10, a depth h1 of the groove 3 that constitutes the flow path 3 is not particularly limited as long as the depth is large enough for a fluid to be capable of flowing through the groove 3, and examples of the thickness include 100 μm to 1000 μm.

In the fluidic device 10, a height h2 of the protrusion part 4 is not particularly limited as long as the height is large enough for a fluid to be capable of passing through the flow path having a height of h1-h2, and examples of the height include 50 μm to 500 μm.

In the fluidic device 10, the depth of the flow path 3 in the valve structure represented by the difference "h1-h2" is not particularly limited as long as a fluid can flow through the flow path 3, and examples of the depth include 50 μm to 500 μm.

In the fluidic device 10, the length W1 along the flow path 3 of the protrusion part 4 is not particularly limited, and examples of the length W1 include 3 mm to 5 mm.

In the fluidic device 10, the length W2 from the first fixation part B1 to the second fixation part B2 is not particularly limited, and examples of the length W2 include 1 mm to 3 mm.

In the fluidic device 10, the length W3 of the base structure 6 is not particularly limited, and examples of the length W3 include 0.5 mm to 3 mm.

In the fluidic device 10, the length in the width direction of the groove 3 that constitutes the flow path 3 is not particularly limited as long as the length is large enough for a fluid to be capable of flowing through the groove 3, and examples of the length include 100 μm to 1000 μm.

The route of the flow path 3 can be appropriately designed and may include a branch point in the route of the flow path 3 or may have a merging point at which a plurality of branched flow paths merge.

An embodiment of the present invention is a fluidic device including a valve configured to adjust a fluid flow in the first direction F of the flow path 3, the fluidic device including: the diaphragm D of the valve; the first substrate 1 having the groove 3 that constitutes the flow path 3 and the protrusion part 4 at a position facing the diaphragm D in the groove 3; and the second substrate 2 to which the diaphragm D is fixed, wherein an end part (first end part 4a) positioned on the most upstream side of the flow path 3 of the protrusion part 4 is located at a more upstream position than a fixation part (first fixation part B1) on the most upstream side to which the diaphragm D is fixed.

<<Fluid Control Method>>

A first embodiment of a fluid control method according to the present invention is a fluid control method in the fluidic device 10 described above. In the fluid control method of the present embodiment, a liquid in each flow path can be driven, for example, by an external pump.

The fluidic device 10 is a fluidic device including: the diaphragm D of the valve; the first substrate 1 having the groove 3 that constitutes the flow path 2 and the protrusion part 4 at a position facing the diaphragm D of the groove 3; and the second substrate 2 to which the diaphragm D is fixed at the first fixation part B1 and the second fixation part B2, wherein the length W1 from the first end part 4a of the protrusion part 4 to the second end part 4b of the protrusion part 4 seen in the first direction F of the flow path 3 is greater than the length W2 from the first fixation part B1 to the second fixation part B2.

The fluidic device 10 includes: the first substrate 1 in which the groove 3 having a depth h1 that constitutes the flow path 3 is formed on the first surface 1a; the second substrate 2 in which the base structure 6 that constitutes the valve is formed on the second surface 2a; and a elastomer sheet 5 that constitutes the diaphragm D of the valve and is sandwiched between the first surface 1a of the first substrate 1 and the second surface 2a of the second substrate 2.

In the fluidic device 10, the protrusion part 4 having a height h2 is formed at a position facing the base structure 6 of the groove 3. The height of the flow path 3 in the valve is h1-h2, and the length W1 from the first end part 4a of the protrusion part 4 to the second end part 4b of the protrusion part 4 seen in the extension direction of the groove 3 is greater than the length W3 of the base structure 6 seen in the extension direction of the groove 3.

In the first embodiment of the control method, at least the following four Steps A to D are performed (refer to FIG. 4).

Step A is a step in which the diaphragm D formed of the elastomer sheet 5 positioned immediately above the base structure 6 is deformed and is pressed to the top surface 4c of the protrusion part 4.

Step B is a step in which a fluid including gas G and liquid S is introduced to the flow path 3 constituted by the groove 3, and the fluid is delivered until a front end SF of the liquid S arrives before the protrusion part 4.

Step C is a step in which by reducing the deformation amount of the diaphragm D to thereby reduce an added pressure to the protrusion part 4 according to the diaphragm D, the front end SF of the liquid S is stopped by the protrusion part 4, and only gas G that is present between the protrusion part 4 and the front end SF of the liquid S is allowed to pass.

Step D is a step in which by further reducing or releasing the deformation amount of the diaphragm D, thereby the liquid S that has been stopped by the protrusion part 4 is allowed to pass.

As an example, when the base structure 6 is the hole 6, in Step A, the inside of the hole 6 formed of the inner side surfaces 6a, 6b is made to be in a positive pressure, and thereby, it is possible to expand the elastomer sheet 5 that functions as the diaphragm D. In this case, by expanding the elastomer sheet 5 until part of the elastomer sheet 5 comes into contact with the protrusion part 4, it is possible to reliably stop the flow of the liquid S.

As an example, when the base structure 6 is the hole 6, in Step C, by relaxing the positive pressure inside the hole 6, only gas G that is present between the first end part 4a of the protrusion part 4 and the front end SF of the liquid S is allowed to pass, and the gas G is allowed to flow to the more downstream flow path 3 than the second end part 4b of the protrusion part 4. In this case, the expansion of the elastomer sheet 5 is not completely released to maintain about half of the expansion, and thereby, it is possible to sufficiently prevent the liquid S from passing through the protrusion part 4. The expansion of the elastomer sheet 5 can be reduced such that a gap through which the gas G can pass is formed between the top of the expansion of the elastomer sheet 5 and the protrusion part 4. Further, in Step D, by further relaxing or releasing the positive pressure inside the hole 6 to further reduce or completely release the expansion of the elastomer sheet 5, the liquid S passes through the protrusion part 4 and flows to the downstream side of the flow path 3.

In Step A, when the diaphragm D formed of the elastomer sheet 5 comes into contact with the protrusion part 4, the deformation amount of the diaphragm D seen in the height direction (depth direction) of the groove 3 can be at least a height h3 obtained by subtracting the height h2 of the protrusion part 4 from the height h1 of the groove 3. When the deformation amount of the elastomer sheet 5 is measured, a deformation amount before and after the deformation at an arbitrary point of the elastomer sheet 5 may be measured. In the example of FIG. 4, h3 is the same as h1-h2.
<<Fluidic Device (2)>>

Second Embodiment

Figure 8:
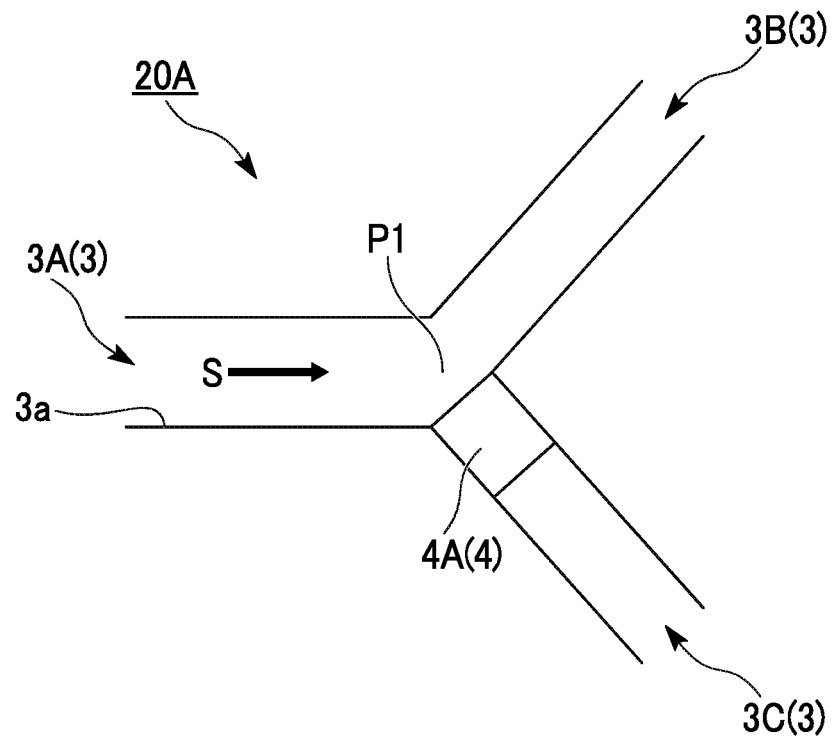
FIG. 8 is a schematic view showing a configuration of flow paths seen in which the first substrate and the second substrate that constitute the fluidic device are overlapped in the thickness direction of the substrates.

As shown in FIG. 8, a second embodiment of a fluidic device according to the present invention is a fluidic device 20A including a valve that adjusts a fluid flow in a flow path 3. Since the fundamental configuration of the fluidic device 20A is the same as the fluidic device 10, the same reference numerals are given to the same configuration, and redundant descriptions are omitted.

The fluidic device 20A is a fluidic device including a valve that adjusts a fluid flow in a flow path. The fluidic device 20A includes a branch route in which a first flow path 3A (3), a second flow path 3B (3), and a third flow path 3C (3) are connected to each other at a single branch point P1. The fluidic device 20A includes the first substrate 1 in which the groove 3 having a depth h1 that constitutes the branch flow path is formed on the first surface 1a and the second substrate 2 having the second surface 2a. In the fluidic device 20A, the depth of the groove that constitutes the first to third flow paths 3A to 3C is h1, and a first protrusion part 4A (4) having a height h2 is formed on the groove 3 that constitutes the vicinity of the branch point P1 such that the third flow path 3C is shallowed in the vicinity of the branch point P1. A first end part of the first protrusion part 4A is provided in the vicinity of the branch point P1, and therefore liquid is prevented from accumulating in the vicinity of the branch point P1 in the third flow path 3C.

The second flow path 3B includes at least one valve (not shown) that adjusts a fluid flow in the flow path. The third flow path 3C may include at least one valve that adjusts a fluid flow in the flow path. The first flow path 3A may include at least one valve that adjusts a fluid flow in the flow path.

The valve included in the fluidic device 20A is not particularly limited as long as the valve can control the fluid flow in a predetermined flow path of the first flow path 3A, the second flow path 3B, and the third flow path 3C. Examples of the valve include the above-described valve structure in the fluidic device 10 of the first embodiment. The valve structure includes at least the base structure 6 formed on the second surface 2a of the second substrate 2 and the sheet 5 that constitutes the diaphragm D of the valve and is sandwiched between the first surface 1a of the first substrate 1 and the second surface 2a of the second substrate 2.

In the fluidic device 20A, by introducing first liquid S1 from a first end part 3a of the first flow path 3A to make the second flow path 3B to be in a negative pressure, the first liquid S1 passes through the branch point P1 and flows into the second flow path 3B. In this case, the first protrusion part 4A is provided in the vicinity of the branch point P1 of the third flow path 3C, and therefore, the first liquid S does not easily flow into the third flow path 3C. Even if the valve is not provided on the third flow path 3C, and the third flow path 3C is released to the atmospheric pressure, it is prevented that the first liquid S1 flows into the third flow path 3C according to the flow path resistance of the first protrusion part 4A.

In this way, the first protrusion part 4A is provided, and thereby, it is possible to control the fluid flow in the flow path.

Third Embodiment

Figure 9:
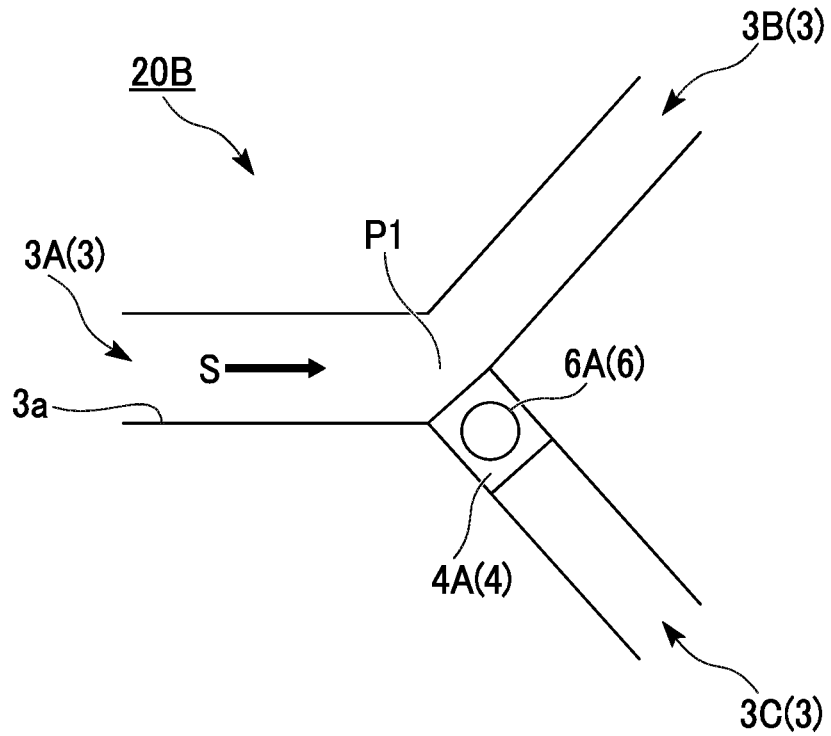
FIG. 9 is a schematic view showing a configuration of flow paths seen in which the first substrate and the second substrate that constitute the fluidic device are overlapped in the thickness direction of the substrates.

As shown in FIG. 9, a third embodiment of a fluidic device according to the present invention is a fluidic device 20B including a valve that adjusts a fluid flow in a flow path 3. Since the fundamental configuration of the fluidic device 20B is the same as the fluidic device 20A, the same reference numerals are given to the same configuration, and redundant descriptions are omitted.

In the fluidic device 20B, the depth of the groove that constitutes the first to third flow paths 3A to 3C is h1, and a first protrusion part 4A (4) having a height h2 is formed on the groove 3 that constitutes the vicinity of the branch point P1 such that the third flow path 3C is shallowed in the vicinity of the branch point P1. A first end part of the first protrusion part 4A is provided in the vicinity of the branch point P1, and therefore, liquid is prevented from accumulating in the vicinity of the branch point P1 in the third flow path 3C.

In the fluidic device 20B, the diaphragm D and the base structure 6 are formed at a position facing the first protrusion part 4A provided on the groove 3 that constitutes the third flow path 3C. The groove 3 is formed on the first surface 1a of the first substrate 1, and the base structure 6 is formed on the second surface 2a of the second substrate 2. When seen in the overlapping direction (thickness direction of the substrates) of the first substrate 1 and the second substrate 2, the first protrusion part 4A and the base structure 6 overlap with each other.

The sheet 5 immediately above the base structure 6 functions as the diaphragm D. The sheet 5 is, for example, an elastomer sheet. When the diaphragm D is deformed and is pressed to the first protrusion part 4A, the valve structure becomes a closed structure. The open structure and the closed structure of the valve are similar to those of the above-described value of the fluidic device 10 of the first embodiment. In the fluidic device 20B, by introducing liquid S from a first end part 3a of the first flow path 3A to make the second flow path 3B to be in a negative pressure, the liquid S passes through the branch point P1 and flows into the second flow path 3B. In this case, a flow path resistance of the first protrusion part 4A provided in the vicinity of the branch point P1 of the third flow path 3C is present, and therefore, the liquid S does not easily flow into the third flow path 3C. Further, when the valve formed of the base structure 6, the sheet 5, and the first protrusion part 4A is the closed structure, it is reliably prevented that the liquid S flows into the third flow path 3C. In this way, the first protrusion part 4A, the sheet 5, and the base structure 6 are provided, and thereby, it is possible to control the fluid flow in the flow path.

Fourth Embodiment

Figure 10:
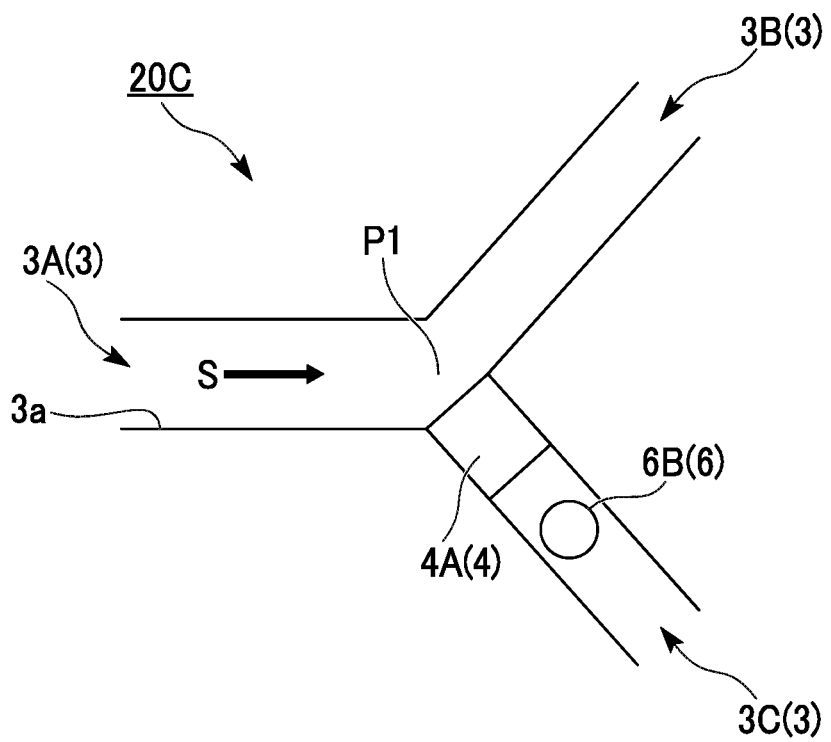
FIG. 10 is a schematic view showing a configuration of flow paths seen in which the first substrate and the second substrate that constitute the fluidic device are overlapped in the thickness direction of the substrates.

As shown in FIG. 10, a fourth embodiment of a fluidic device according to the present invention is a fluidic device 20C including a valve that adjusts a fluid flow in a flow path 3. Since the fundamental configuration of the fluidic device 20C is the same as the fluidic device 20B, the same reference numerals are given to the same configuration, and redundant descriptions are omitted.

In the fluidic device 20C, the depth of the groove that constitutes the first to third flow paths 3A to 3C is h1, and a first protrusion part 4A (4) having a height h2 is formed on the groove 3 that constitutes the vicinity of the branch point P1 such that the third flow path 3C is shallowed in the vicinity of the branch point P1. A first end part of the first protrusion part 4A is provided in the vicinity of the branch point P1, and therefore, liquid is prevented from accumulating in the vicinity of the branch point P1 in the third flow path 3C.

In the fluidic device 20C, the base structure 6 is formed on the downstream side of the first protrusion part 4A at a position away from the branch point P1 and a position facing the first protrusion part 4A provided on the groove 3 that constitutes the third flow path 3C. That is, in the third flow path 3C, the first protrusion part 4A is provided at a position closer to the branch point P1 than the base structure 6. The groove 3 is formed on the first surface 1a of the first substrate 1, and the base structure 6 is formed on the second surface 2a of the second substrate 2. When seen in the overlapping direction (thickness direction of the substrates) of the first substrate 1 and the second substrate 2, the first protrusion part 4A and the base structure 6 do not overlap with each other.

The sheet 5 immediately above the base structure 6 functions as the diaphragm D. The sheet 5 is, for example, an elastomer sheet. When the diaphragm D is deformed, falls inside the groove 3 that constitutes the third flow path 3C, and is pressed to the bottom surface of the groove 3, the valve structure becomes a closed structure.

The open structure and the closed structure of the valve are similar to those of the above-described value of the fluidic device 10 of the first embodiment other than that, in the closed structure, the sheet 5 is pressed to the bottom surface 3c of the groove 3 in place of the top surface 4c of the protrusion part 4.

In the fluidic device 20C, by introducing liquid S from a first end part 3a of the first flow path 3A to make the second flow path 3B to be in a negative pressure, the liquid S passes through the branch point P1 and flows into the second flow path 3B. In this case, a flow path resistance of the first protrusion part 4A provided in the vicinity of the branch point P1 of the third flow path 3C is present, and therefore, the liquid S does not easily flow into the third flow path 3C. Further, when the valve formed of the base structure 6 and the sheet 5 is the closed structure, it is reliably prevented that the liquid S flows into the third flow path 3C. In this way, the first protrusion part 4A, the sheet 5, and the base structure 6 are provided, and thereby, it is possible to control the fluid flow in the flow path.

When the valve structure of the fluidic device 20B of the second embodiment and the valve structure of the fluidic device 20C of the third embodiment are compared, since the deformation amount of the sheet 5 is smaller in the valve of the fluidic device 20B in which the base structure 6 is provided at a position facing the first protrusion part 4A, the response is faster, and it is possible to more reliably prevent the flow-in of the liquid S.

Fifth Embodiment

Figure 11:
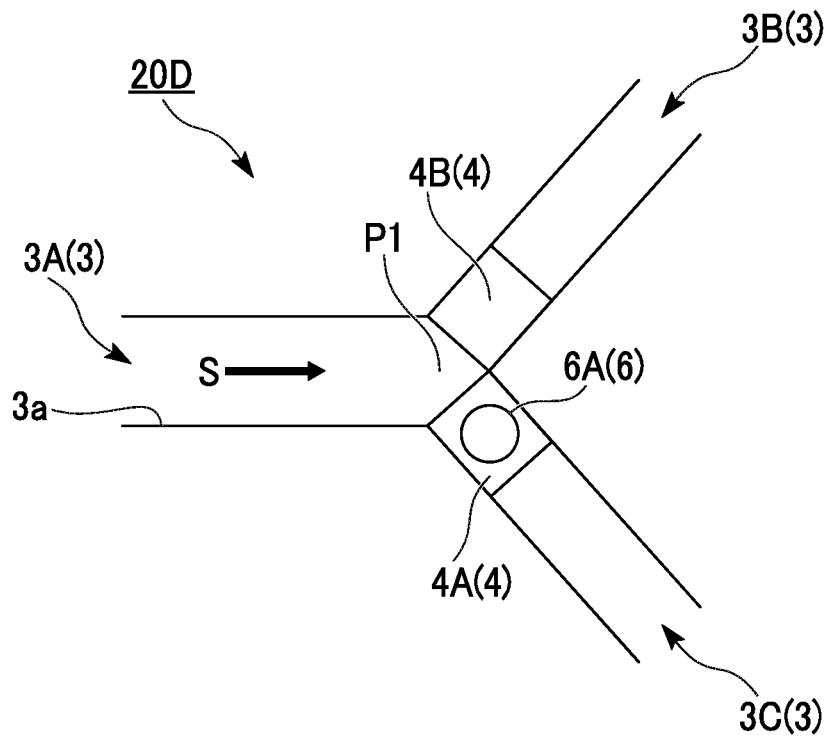
FIG. 11 is a schematic view showing a configuration of flow paths seen in which the first substrate and the second substrate that constitute the fluidic device are overlapped in the thickness direction of the substrates.

As shown in FIG. 11, a fifth embodiment of a fluidic device according to the present invention is a fluidic device 20D including a valve that adjusts a fluid flow in a flow path 3. Since the fundamental configuration of the fluidic device 20D is the same as the fluidic device 20B, the same reference numerals are given to the same configuration, and redundant descriptions are omitted.

In the fluidic device 20D, the depth of the groove that constitutes the first to third flow paths 3A to 3C is h1, and a first protrusion part 4A (4) having a height h2 is formed on the groove 3 that constitutes the vicinity of the branch point P1 such that the third flow path 3C is shallowed in the vicinity of the branch point P1. A first end part of the first protrusion part 4A is provided in the vicinity of the branch point P1, and therefore, liquid is prevented from accumulating in the vicinity of the branch point P1 in the third flow path 3C.

Further, a second protrusion part 4B (4) having a height h2' is formed on the groove 3 that constitutes the vicinity of the branch point P1 such that the second flow path 3B is shallowed in the vicinity of the branch point P1. A first end part of the second protrusion part 4B is provided in the vicinity of the branch point P1, and therefore, liquid is prevented from accumulating in the vicinity of the branch point P1 in the second flow path 3B.

The height h2' of the second protrusion part 4B may be the same as or may be different from the height h2 of the first protrusion part 4A. The length along the second flow path 3B of the second protrusion part 4B may be the same as or may be different from the length along the third flow path 3C of the first protrusion part 4A.

In the fluidic device 20D, by introducing liquid S from a first end part 3a of the first flow path 3A to make the second flow path 3B to be in a negative pressure, the liquid S passes through the branch point P1 and flows into the second flow path 3B. In this case, a flow path resistance of the first protrusion part 4A and a flow path resistance of the second protrusion part 4B provided in the vicinity of the branch point P1 are present, and therefore, the liquid S does not easily flow into both of the third flow path 3C and the second flow path 3B. When the valve provided on the third flow path 3C is closed to thereby relatively decrease the flow path resistance of the second flow path 3B, the fluid S flows into the second flow path 3B.

After the liquid S flows into the second flow path 3B, by stopping the operation by which the second flow path 3B is made to be in a negative pressure, it is possible to stop the liquid S at the branch point P1. In a state where the liquid S is stopped at the branch point P1, by allowing second liquid S2 that is different from the liquid S (hereinafter, referred to as first liquid S1) to flow into the branch point P1 via the first end part 3a of the first flow path 3A following the first liquid S1, the first liquid S1 and the second liquid S2 diffuse to each other and are mixed at the branch point P1.

In this way, the first protrusion part 4A and the second protrusion part 4B are provided in the vicinity of the branch point P1, and thereby, a plurality of liquids differing from each other can be mixed at the branch point P1.

<Regarding Residual of Liquid at Branch Point P1 and in Vicinity of Branch Point P1>

In the fluidic devices 20A to 20D of the second embodiment to the fifth embodiment, by introducing first liquid S1 from the first end part 3a of the first flow path 3A, subsequently stopping the introduction, and then allowing the first liquid S1 that remains in the branch point P1 to fully flow into the second flow path 3B, the branch point P1 and the vicinity of the branch point P1 become a clear state in which the first liquid S1 does not remain. Then, by introducing the second liquid S2 from the first end part 3a of the first flow path 3A, the second liquid S2 can pass through the branch point P1 and flow into the second flow path 3B or the third flow path 3C without the first liquid S1 that is first introduced and the second liquid S2 that is subsequently introduced being mixed.

On the other hand, in a case where the first protrusion part is not provided or the first protrusion part is provided at a position away from the branch point P1 and on the downstream side of the third flow path 3C, when the first liquid S1 flows into the second flow path 3B, a small amount of the first liquid S1 enters the third flow path 3C from the branch point P1, and there is a possibility that a small amount of the first liquid S1 is trapped between the branch point P1 and the first protrusion part. In a state where the first liquid S1 is trapped, when the second liquid S2 is introduced from the first end part 3a of the first flow path 3A, there is a possibility that the trapped first liquid S1 and the second liquid S2 are mixed at the branch point P1 and in the vicinity of the branch point P1. When it is not desired to mix the first liquid S1 and the second liquid S2, the above-described mix may be a problem.

<<Nucleic Acid Purification Method>>

An example of embodiments of a nucleic acid purification method using any of the fluidic devices 20A to 20D of the second to fifth embodiments is described. Cell breakage liquid including nucleic acid is introduced from the first end part 3a of the first flow path 3A. By making the second flow path 3B to be in a negative pressure, the cell breakage liquid is suctioned. The cell breakage liquid passes through a known nucleic acid adsorption body (for example, glass mesh, silica beads group, or the like; hereinafter, a case of glass mesh is described) provided on the first flow path 3A immediately before the branch point P1 and flows into the second flow path 3B. The nucleic acid included in the cell breakage liquid is adsorbed to the glass mesh.

The cell breakage liquid is discharged to the downstream side of the second flow path 3B.

Subsequently, a wash solution is introduced from the first end part 3a of the first flow path 3A. By making the second flow path 3B to be in a negative pressure, the wash solution is suctioned. The wash solution passes through the glass mesh provided on the first flow path 3A immediately before the branch point P1, washes away foreign substances other than the nucleic acid adsorbed to the glass mesh, and flows into the second flow path 3B. The wash solution is completely discharged to the downstream side of the second flow path 3B.

Next, the wash solution is introduced from the first end part 3a of the first flow path 3A. By making the second flow path 3B to be in a negative pressure, the wash solution is suctioned. The wash solution passes through the glass mesh provided on the first flow path 3A immediately before the branch point P1, washes away foreign substances other than the nucleic acid adsorbed to the glass mesh, and flows into the second flow path 3B. The wash solution is completely discharged to the downstream side of the second flow path 3B. The flow path is cleaned up from the first end part 3a of the first flow path 3A to the vicinity of the branch point P1 according to the wash solution passing.

Finally, an eluate is introduced from the first end part 3a of the first flow path 3A. By closing the valve of the second flow path 3B and making the third flow path 3C to be in a negative pressure, the eluate is suctioned. The eluate passes through the glass mesh provided on the first flow path 3A immediately before the branch point P1, elutes the nucleic acid adsorbed to the glass mesh, and flows into the third flow path 3C. The eluate including the nucleic acid as a target is recovered at the downstream side of the third flow path 3C. In the sequence of the purification method of the nucleic acid, since the eluate does not come into contact with the cell breakage liquid and does not substantially come into contact with the wash solution, it is possible to obtain a nucleic acid eluate having a high degree of purification without foreign substances mixing in the eluate.

<<Fluid Control Method (2)>>

A second embodiment of a fluid control method according to the present invention is a fluid control method in any of the above-described fluidic devices 20A to 20D of the second to fifth embodiments and includes at least Step A to Step C described below.

Step A is a step of, by making the inside of the second flow path 3B to be in a negative pressure to thereby introduce first liquid from the first end part 3a of the first flow path 3A, allowing the first liquid to pass through the branch point P1 to be delivered to the second flow path 3B, and preventing the first liquid from flowing into the third flow path 3C from the branch point P1 according to a flow path resistance of the first protrusion part 4A provided on the third flow path 3C.

Step B is a step of, following Step A, allowing the first liquid that is present in the first flow path 3A and the branch point P1 to fully flow to the downstream side of the second flow path 3B.

Step C is a step of, following Step B, by making the inside of the third flow path 3C to be in a negative pressure to thereby introduce second liquid from the first flow path 3A, allowing the second liquid to pass through the branch point P1 to be delivered to the third flow path 3C.

According to the fluid control method of the second embodiment, in Step A, it is possible to prevent the first liquid from flowing into the third flow path 3C from the branch point P1 according to the flow path resistance of the first protrusion part 4A and maintain a clean state of the third flow path 3C. In step A, by closing the valve provided on the third flow path 3C, it is possible to further reliably prevent the first liquid from flowing into the third flow path 3C.

According to the fluid control method of the second embodiment, in Step B, by allowing the first liquid that is present in the first flow path 3A and the branch point P1 to fully flow to the downstream side of the second flow path 3B, the first liquid do not remain in the first flow path 3A and the branch point P1, and the first flow path 3A and the branch point P1 can be made to approach to a clean state.

Following Step B, in Step C, the second liquid is introduced to the clean first flow path 3A and branch point P1, and it is possible to allow the second liquid to flow into the third flow path 3C without causing mixing of the first liquid to the second liquid. In Step C, it is possible to further reliably prevent the second liquid from flowing into the second flow path 3B from the branch point P1 according to the flow path resistance of the second protrusion part 4B provided on the second flow path 3B. Further, in Step C, by closing the valve provided on the second flow path 3B, it is possible to still further reliably prevent the second liquid from flowing into the second flow path 3B from the branch point P1. In the fluid control method of the present embodiment, the liquid in each flow path can be driven by an external pump.

<<Fluidic Device (3)>>

Sixth Embodiment

Figure 12:
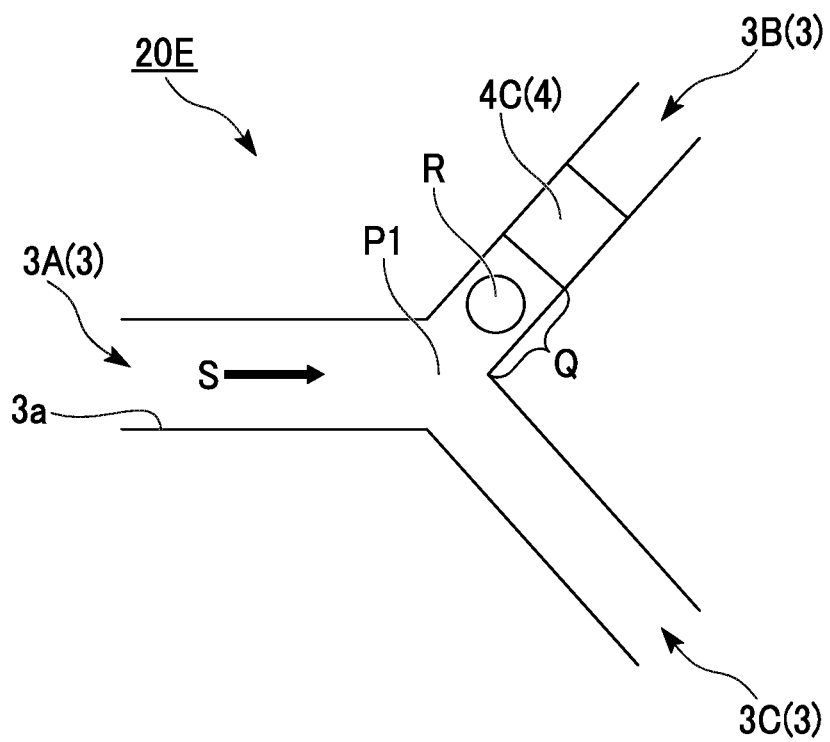
FIG. 12 is a schematic view showing a configuration of flow paths seen in which the first substrate and the second substrate that constitute the fluidic device are overlapped in the thickness direction of the substrates.

As shown in FIG. 12, a second embodiment of a fluidic device according to the present invention is a fluidic device 20E including a valve that adjusts a fluid flow in a flow path 3. Since the fundamental configuration of the fluidic device 20E is the same as the fluidic device 10, the same reference numerals are given to the same configuration, and redundant descriptions are omitted.

The fluidic device 20E is a fluidic device including a valve that adjusts a fluid flow in a flow path. The fluidic device 20E includes a branch route in which a first flow path 3A (3), a second flow path 3B (3), and a third flow path 3C (3) are connected to each other at a single branch point P1. The fluidic device 20E includes the first substrate 1 in which the groove 3 having a depth h1 that constitutes the branch flow path is formed on the first surface 1a and the second substrate 2 having the second surface 2a.

In the fluidic device 20E, the depth of the groove that constitutes the first to third flow paths 3A to 3C is h1 excluding a protrusion part 4C (4) of the second flow path 3B. The second flow path 3B includes a flow path 3 having a length W5 that constitutes a liquid reservoir part Q in the vicinity of the branch point P1. The second flow path 3B includes the protrusion part 4C having a height h2 following the liquid reservoir part Q. That is, the flow path 3 between the branch point P1 and the protrusion part 4C is the liquid reservoir part Q. The configuration of the protrusion part 4C is the same as the above-described configurations of the protrusion parts 4A to 4B other than that the protrusion part 4C is provided at a position away from the branch point P1.

The flow path 3 that constitutes the liquid reservoir part Q may include a predetermined reagent. The type or formulation of the reagent is not particularly limited, and examples of the reagent include a hydrophilic or lipophilic dried reagent having a powder form or a pellet form.

A method of arranging the reagent on the liquid reservoir part Q is not particularly limited, and examples of the method include a method of forming the groove 3 that constitutes the flow path 3 on the first surface 1a of the first substrate 1 that constitutes the flow device 20E and then arranging the reagent inside the groove 3 that corresponds to the liquid reservoir part Q. Then, by bonding the second substrate 2 to the first substrate 1, it is possible to manufacture the flow device 20E. In this way, the method of arranging a predetermined reagent or the like on the groove 3 of the flow path 3 before bonding the substrates can be also applied to the manufacture of a testing device described below.

The second flow path 3B includes at least one valve (not shown) that adjusts a fluid flow in the flow path. The third flow path 3C may include at least one valve that adjusts a fluid flow in the flow path. The first flow path 3A may include at least one valve that adjusts a fluid flow in the flow path.

The valve included in the fluidic device 20E is not particularly limited as long as the valve can control the fluid flow in a predetermined flow path of the first flow path 3A, the second flow path 3B, and the third flow path 3C. Examples of the valve include the above-described valve structure in the fluidic device 10 of the first embodiment. The valve structure includes at least the base structure 6 formed on the second surface 2a of the second substrate 2 and the sheet 5 that constitutes the diaphragm D of the valve and is sandwiched between the first surface 1a of the first substrate 1 and the second surface 2a of the second substrate 2.

The length W5 along the extension direction of the flow path 3 that constitutes the liquid reservoir part Q is not particularly limited. As the fluidic device 20 includes the liquid reservoir part Q, a fluid control method as described next can be realized.

<<Fluid Control Method (3)>>

A third embodiment of a fluid control method according to the present invention is a fluid control method in the above-described fluidic device 20E and includes at least Step A to Step C described below.

Figure 13A:
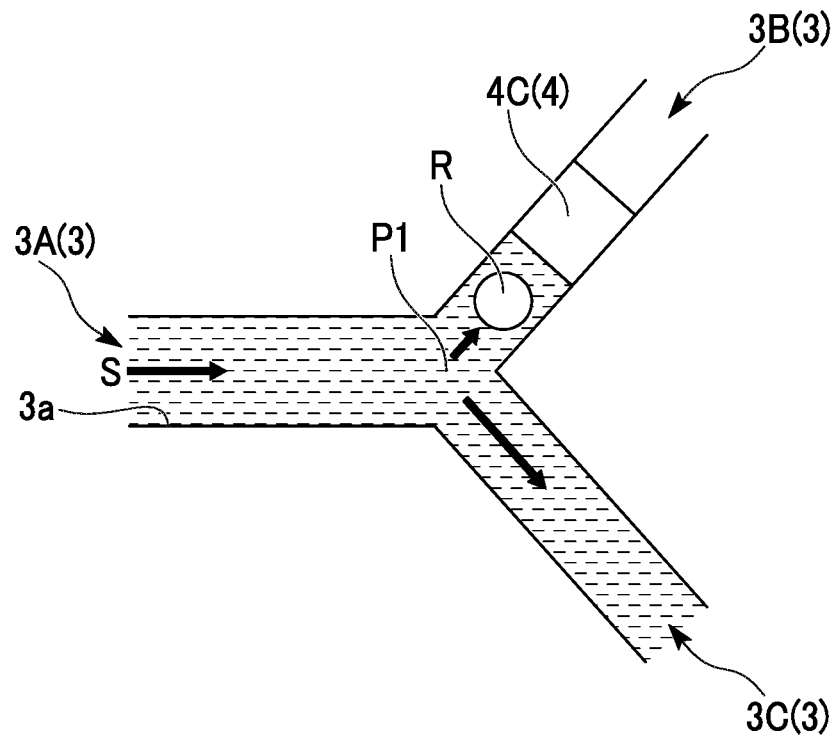
FIG. 13A is a schematic view seen in the substrate thickness direction showing an example of a fluid control method in the fluidic device.

Step A is a step of, by introducing first liquid S from the first end part 3a of the first flow path 3A, allowing the first liquid S to pass through the branch point P1 to be delivered to the third flow path 3C, and by allowing part of the first liquid to enter the liquid reservoir part Q in the second flow path 3B from the branch point P1, stopping the entering before the protrusion part 4C (refer to FIG. 13A).

Figure 13B:
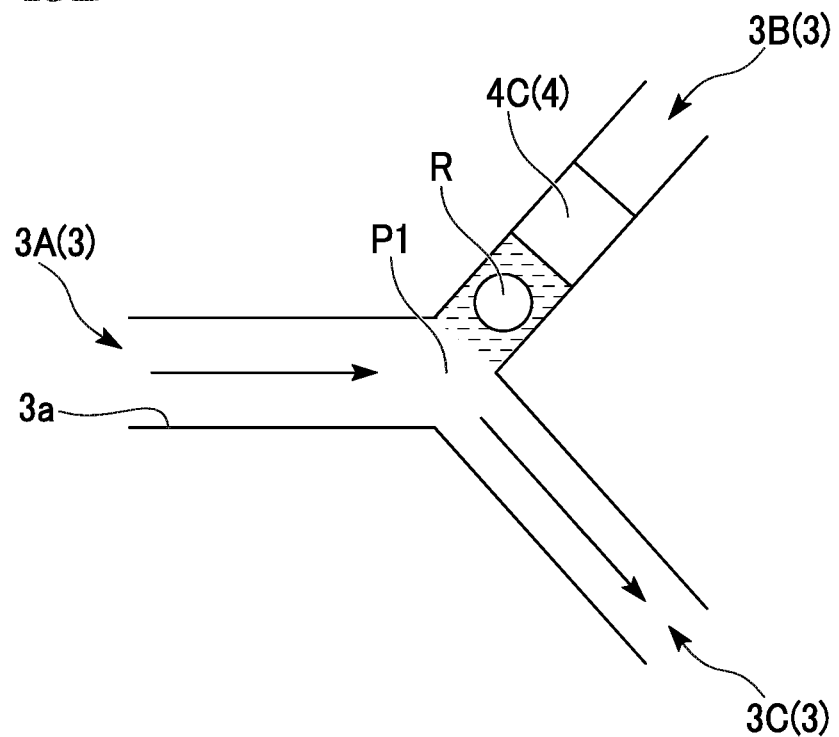
FIG. 13B is a schematic view seen in the substrate thickness direction showing the example of the fluid control method in the fluidic device.

Step B is a step of, following Step A, allowing the first liquid S that is present in the first flow path and the branch point to fully flow into the third flow path (refer to FIG. 13B).

Figure 13C:
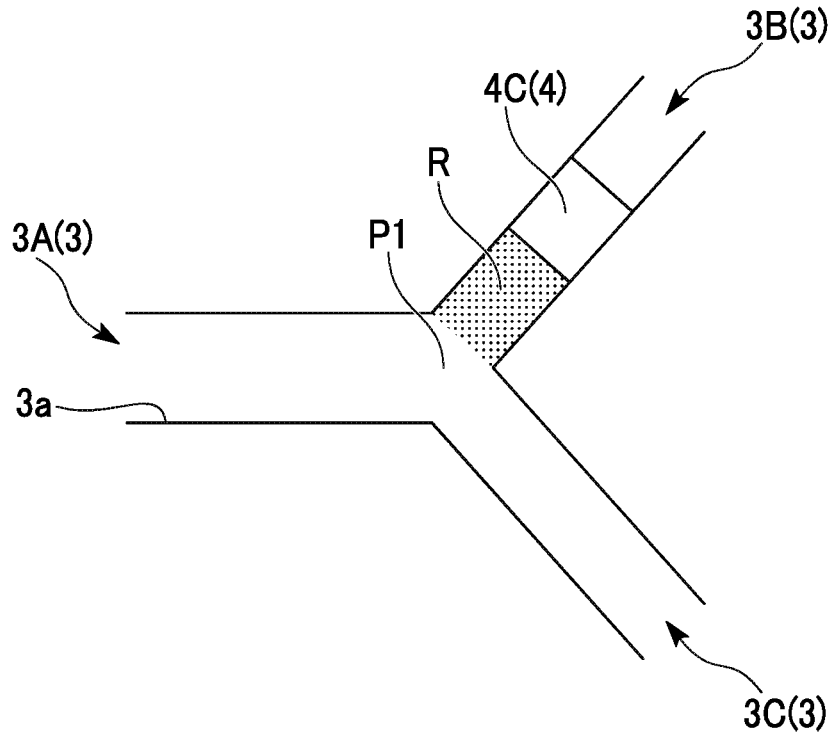
FIG. 13C is a schematic view seen in the substrate thickness direction showing the example of the fluid control method in the fluidic device.

Step C is a step of, following Step B, recovering the part of the first liquid that has been stopped at the liquid reservoir part Q (refer to FIG. 13C).

In Step A, the method of introducing the first liquid S is not particularly limited, and examples of the method include a method of making the third flow path 3C to be in a negative pressure. The first liquid S arriving at the branch point P1 flows into the third flow path 3C in a negative pressure, and part of the first liquid S enters the liquid reservoir part Q of the second flow path 3B according to capillarity or the wetting property of the groove or taking advantage of the momentum of the flow to the third flow path 3C. In this case, part of the first liquid S may be suctioned to the liquid reservoir part Q by making the second flow path 3B to be in a negative pressure. In the fluid control method of the present embodiment, the liquid in each flow path can be driven by an external pump.

The first liquid S that has entered the liquid reservoir part Q is stopped before a first end part of the protrusion part 4C according to the flow path resistance of the protrusion part 4C. When a reagent R is provided at the liquid reservoir part Q, the reagent R comes into contact with the first liquid S, and the reagent R can dissolve.

In Step B, excluding part of the first liquid S that has entered the liquid reservoir part Q, by allowing the first liquid S1 that is present in the first flow path 3A and the branch point P1 to fully flow to the downstream side of the third flow path 3C, the first flow path 3A and the vicinity of the branch point P1 is made to be in a clear state. In this case, by introducing gas such as air and inert gas or liquid that does not easily mix with the first liquid S from the first end part 3a of the first flow path 3A to allow the gas or liquid to flow to the third flow path 3C, it is possible to level the first liquid S that has accumulated in the liquid reservoir part Q at the boundary between the liquid reservoir part Q and the branch point P1. According to the leveling, the volume of the first liquid S that comes into contact with the reagent R at the liquid reservoir part Q becomes the same as the volume of the liquid reservoir part Q. A predetermined concentration of a reagent solution can be obtained by dissolving the reagent R into a predetermined volume of the first liquid S.

In Step C, the method of recovering the part of the first liquid S or the reagent solution that has been stopped at the liquid reservoir part Q from the liquid reservoir part Q is not particularly limited. As an example, by making the downstream side of the second flow path 3B to be in a negative pressure, the part of the first liquid S or the reagent solution passes through the protrusion part 4, and it is possible to recover the liquid at the downstream side of the second flow path 3B. The recovered liquid may flow into a flow path connected to the downstream side of the second flow path 3B.

<<Fluidic Device (4)>>

Seventh Embodiment

Figure 14:
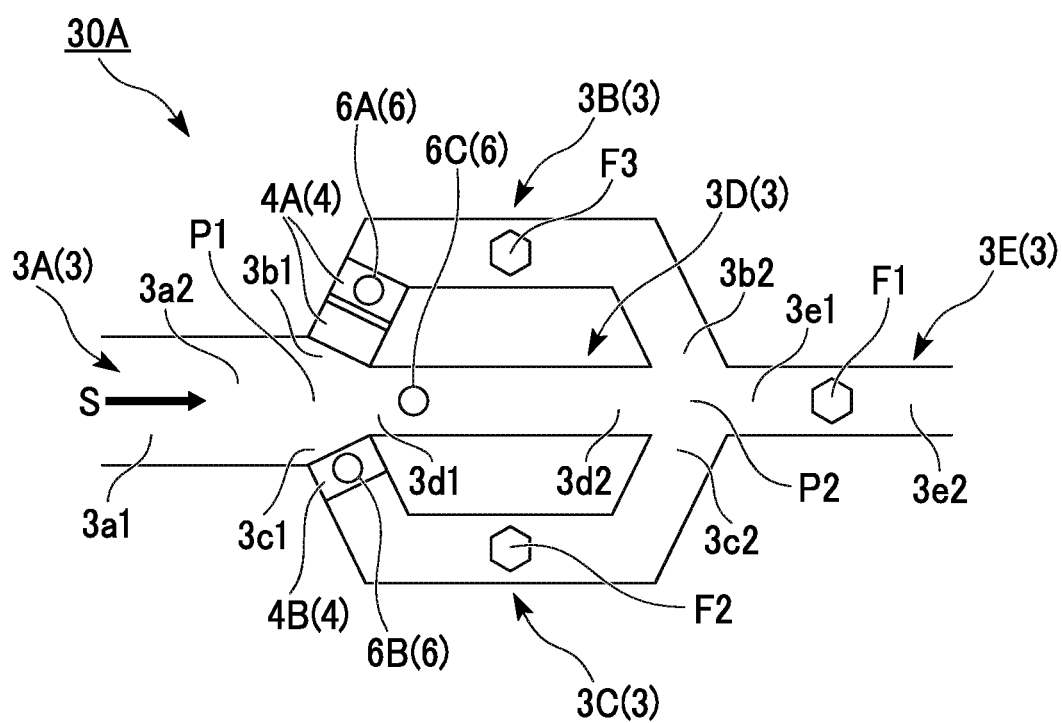
FIG. 14 is a schematic view showing a configuration of flow paths seen in which the first substrate and the second substrate that constitute the fluidic device (testing device) are overlapped in the thickness direction of the substrates.

As shown in FIG. 14, a seventh embodiment of a fluidic device according to the present invention is a fluidic device 30A including a valve that adjusts a fluid flow in a flow path 3. Since the fundamental configuration of the fluidic device 30A is the same as the fluidic device 10 and the fluidic devices 20A to 20D, the same reference numerals are given to the same configuration, and redundant descriptions are omitted.

The fluidic device 30A includes: a first substrate 1 in which a groove 3 that constitutes a first to fifth flow paths 3A to 3E (3) is formed on a first surface 1a; a sheet 5 that covers the first surface 1a; and a second substrate 2 having a second surface 2a that is bonded to the first surface 1a via the sheet 5. The sheet 5 is, for example, an elastomer sheet.

The route constituted by the groove 3 formed on the first substrate 1 is formed of a branch route and a merging route. In the branch route, a first end part 3a1 of the first flow path 3A communicates outside, and a second end part 3a2 of the first flow path 3A, a first end part 3b1 of the second flow path 3B, a first end part 3c1 of the third flow path 3C, and a first end part 3d1 of the fourth flow path 3D are connected to each other at a single branch point P1. In the merging route, a second end part 3b2 of the second flow path 3B, a second end part 3c2 of the third flow path 3C, a second end part 3d2 of the fourth flow path 3D, and a first end part 3e1 of the fifth flow path 3E are connected to each other at a single merging point P2, and a second end part 3e2 of the fifth flow path 3E communicates outside.

In the fluidic device 30A, the depth of the groove 3 that constitutes the first to fifth flow paths 3A to 3E is h1. At least one first protrusion part 4A (4) having a height h2 is formed on the bottom surface 3c of the groove 3 that constitutes the vicinity of the branch point P1 such that the second flow path 3B is shallowed in the vicinity of the branch point P1 of the groove 3 that constitutes the second flow path 3B. Further, at least one second protrusion part 4B (4) having a height h3 is formed on the bottom surface 3c of the groove 3 that constitutes the vicinity of the branch point P1 such that the third flow path 3C is shallowed in the vicinity of the branch point P1 of the groove 3 that constitutes the third flow path 3C.

As described above, as the first protrusion part 4A and the second protrusion part 4B are provided, the flow path resistance at the branch point P1 is large in the order of the fourth flow path 3D, the third flow path 3C, and the second flow path 3B. That is, when the liquid introduced to the first end part 3a1 of the first flow path 3A arrives at the branch point P1, a flow path into which the liquid flows the most easily is the fourth flow path 3D, and a flow path into which the liquid flows the second most easily is the third flow path 3C.

In the fluidic device 30A, a row of two first protrusion parts 4A is arranged in the vicinity of the branch point P1 of the second flow path 3B. On the other hand, one second protrusion part 4B is provided in the vicinity of the branch point P1 of the third flow path 3C. The total L1 of lengths along the second flow path 3B of the two first protrusion parts 4A is longer than a length L2 along the third flow path 3C of the second protrusion part 4B. According to the relative relationship between the lengths L1, L2, the flow path resistance of the first protrusion part 4A becomes larger than the flow path resistance of the second protrusion part 4B.

In the fluidic device 30A, an opening part of inner side surfaces constituting a first through-hole 6A, which opens facing the groove 3 constituting the second flow path 3B, is provided in the thickness direction of the second substrate 2. When seen in the overlapping direction (thickness direction) of the first substrate 1 and the second substrate 2, the opening part is provided at a position (overlapping position) facing the first protrusion part 4A which is further away from the branch point P1 of the two first protrusion parts 4A. The first through-hole 6A is an example of the base structure 6 of the valve.

In the fluidic device 30A, an opening part of inner side surfaces constituting a second through-hole 6B, which opens facing the groove 3 constituting the third flow path 3C, is provided in the thickness direction of the second substrate 2. When seen in the overlapping direction (thickness direction) of the first substrate 1 and the second substrate 2, the opening part is provided at a position (overlapping position) facing the second protrusion part 4B. The second through-hole 6B is an example of the base structure 6 of the valve.

In the fluidic device 30A, an opening part of inner side surfaces constituting a third through-hole 6C, which opens facing the groove 3 constituting the fourth flow path 3D, is provided in the thickness direction of the second substrate 2. When seen in the overlapping direction of the first substrate 1 and the second substrate 2, the opening part is provided in the vicinity of the branch point P1. The third through-hole 6C is an example of the base structure 6 of the valve.

By using the fluidic device 30A, it is possible to allow the liquid introduced from the first end part 3a1 of the first flow path 3A to flow into an arbitrary flow path selected from the second flow path 3B, the third flow path 3C, and the fourth flow path 3D. In this case, since the first protrusion part 4A and the second protrusion part 4B are provided in the vicinity of the branch point P1, it is prevented that the liquid enters a flow path other than the selected one flow path. Further, since the first end part of the first protrusion part 4A is provided in the vicinity of the branch point P1, it is prevented that the liquid accumulates at the first end part 3b1 of the second flow path 3B. Similarly, since the first end part of the second protrusion part 4B is provided in the vicinity of the branch point P1, it is prevented that the liquid accumulates at the first end part 3c1 of the third flow path 3C.

<<Testing Device, Testing Method>>

A first embodiment of a testing device according to the present invention is a testing device configured to inspect an inspection target material included in a liquid sample using the fluidic device 30A of the seventh embodiment described above.

In the testing device, a capture part F1 to which a capture material that can be coupled to the inspection target material is fixed is provided at the groove 3 that constitutes the fifth flow path 3E, a first supply part F2 including a detection material that can be coupled to a complex of the inspection target material and the capture material is provided at the groove 3 that constitutes the third flow path 3C, and a second supply part F3 including a signal material configured to emit a signal by which it can be detected that the detection material is present at the capture part F1 is provided at the groove 3 that constitutes the second flow path 3B.

A method of arranging the capture material on the capture part F1 is not particularly limited, and examples of the method include a method of forming the groove 3 that constitutes the flow path 3 on the first surface 1a of the first substrate 1 that constitutes the fluidic device 30A and then arranging the capture material inside the groove 3 that corresponds to the capture part F1. Similarly, the detection material is arranged inside the groove 3 that corresponds to the first supply part F2, and the signal material is arranged inside the groove 3 that corresponds to the second supply part F3. Then, by bonding the second substrate 2 to the first substrate 1, it is possible to manufacture the testing device using the fluidic device 30A.

A first embodiment of a testing method according to the present invention is a method of inspecting an inspection target material included in a liquid sample using the first embodiment of the testing device. In the testing method of the first embodiment, the liquid in each flow path can be driven by an external pump.

The testing method of the first embodiment includes a step of introducing the liquid sample from the first end part 3a1 of the first flow path 3A to arrive at the branch point P1; introducing the liquid sample to the fourth flow path 3D having the smallest flow path resistance among the second flow path 3B, the third flow path 3C, and the fourth flow path 3D to arrive at the merging point P2; and introducing the liquid sample to the fifth flow path 3E connected to the merging point P2, and the inspection target material included in the liquid sample is coupled to the capture material at the capture part F1 provided on the fifth flow path 3E.

The inspection target material included in the liquid sample is not particularly limited and may be a material that is specifically coupled to or may be a material that is non-specifically coupled to the capture material at the capture part F1. Examples of the inspection target material include an antigen. Examples of the capture material include a first antibody (capture antibody) that can be coupled to the antigen. The first antibody can be obtained by an antibody production method. The first antibody is fixed to the groove of the fifth flow path 3E according to a known method and forms the capture part F1. Examples of a solvent that constitutes the liquid sample include a pH buffer solution capable of dissolving or dispersing the antigen.

When foreign substances other than the inspection target material as a target are included in the liquid sample, foreign substances may adhere non-specifically to the capture part F1. In order to wash the foreign substances, following the liquid sample, by introducing a predetermined wash solution into the fifth flow path 3E via the fourth flow path 3D similarly to the liquid sample, the capture part F1 may be washed, and the foreign substances may be washed out. Examples of the wash solution include a solution of the pH buffer solution to which a surfactant is added.

In order to prevent a material other than the inspection target material from adhering non-specifically to the capture part F1, following the wash solution, by introducing a blocking solution into the fifth flow path 3E via the fourth flow path 3D similarly to the liquid sample, the capture part F1 and the first, fourth, and fifth flow paths may be blocked. Examples of the blocking solution include a solution of the wash solution to which a serum albumin is added.

Next, in a state where the fourth flow path 3D is closed, a step is performed in which, by introducing the first liquid from the first end part 3a1 of the first flow path 3A to arrive at the branch point P1 and be introduced to the third flow path 3C having a relatively low flow path resistance, causing the first liquid to contain the detection material at the first supply part F2, and then causing the first liquid to arrive at the merging point P2 to be introduced to the fifth flow path 3E connected to the merging point P2, the detection material is coupled to the inspection target material that has already been captured by the capture material at the capture part F1.

Examples of the method of closing the fourth flow path 3D include a method of, by adding air pressure to the third through-hole 6C to thereby cause the diaphragm D formed of the elastomer sheet 5 to fall inside the fourth flow path 3D, suppressing the fluid flow in the fourth flow path 3D.

Examples of the detection material include a second antibody (detection antibody) that can be coupled to the inspection target material. The second antibody can be obtained by an antibody production method. The first antibody and the second antibody may be the same antibody or may be a different antibody. As an example, an epitope of the first antibody and an epitope of the second antibody are different from each other.

For example, an enzyme that can transform a fluorescence precursor material into a fluorescence material is coupled to the detection antibody. The enzyme labeling of the antibody (conjugate of the antibody and the enzyme) can be performed by a known method. Further, a commercially available enzyme-labeled antibody may be used. The enzyme is not particularly limited, and examples of the enzyme include a peroxidase and an alkaline phosphatase.

The solvent that constitutes the first liquid is not particularly limited and is preferably a solvent capable of dissolving or dispersing the detection material. Examples of the solvent include a pH buffer solution capable of dissolving the detection antibody.

As the capture antibody and the inspection target material are coupled to each other at the capture part F1, and the detection antibody flows into the capture part F1, it is possible to form the capture antibody, the inspection target material, and a complex of the detection antibody and the enzyme.

Next, in a state where the fourth flow path 3D and the third flow path 3C are closed, a step is performed in which, by introducing the second liquid from the first end part 3a1 of the first flow path 3A to arrive at the branch point P1 to be introduced to the second flow path 3B, causing the second liquid to contain the signal material at the second supply part F3, and then causing the second liquid to arrive at the merging point P2 to be introduced to the fifth flow path 3E connected to the merging point P2, the signal material and the detection material that has already been coupled interact with each other at the capture part F1 to generate the signal.

Examples of the method of closing the third flow path 3C include a method of, by adding air pressure to the second through-hole 6B to thereby cause the diaphragm D formed of the elastomer sheet 5 to fall inside the third flow path 3C, suppressing the fluid flow in the third flow path 3C. Examples of the method of closing the fourth flow path 3D include the above-described method.

Examples of the signal material include a fluorescence material precursor as a substrate that is converted into a fluorescence material by the enzyme. Examples of the fluorescence material precursor include tetramethylbenzidine (TMB), o-phenylenediamine (OPD), and 2,2'-azino-bis (3-ethyl benzothiazoline-6-sulfonate ammonium) (ABTS).

The solvent that constitutes the second liquid is not particularly limited and can be a solvent capable of dissolving or dispersing the signal material. Examples of the solvent include a pH buffer solution capable of dissolving the fluorescence material precursor.

At the capture part F1, the complex is fixed to the groove 3 that constitutes the fifth flow path 3E via the capture antibody, and the fluorescence material precursor as an example of the signal material flows into the capture part F1 to thereby generate the fluorescence material according to an enzyme reaction. By externally irradiating the fluorescence material with excitation light, fluorescence is emitted as the signal. By observing the fluorescence according to a known method, it is possible to qualitatively or quantitatively analyze the presence of the inspection target material trapped by the capture part F1.

<Pump Function>

The above-described embodiments of the fluidic device according to the present invention include a single valve or a plurality of valves. By opening and closing a plurality of valves provided in series or in parallel in each flow path or by opening and closing a single valve provided in an arbitrary flow path, the valve can function as a pump that produces a flow of the fluid in the flow path. The type of the valve is not particularly limited, and examples of the valve include a diaphragm valve described above. The diaphragm of the valve is provided, for example, at a position facing the protrusion part 4 included in the groove 3 described above.

As an example, by synchronously controlling the opening and closing of the plurality of valves, waves are generated from the fluid in the flow path, and it is possible to allow the fluid to flow in a predetermined direction. For example, in preferably two or more valves and in more preferably three or more valves serially arranged in the flow path, the fluid in the flow path can be delivered in a predetermined direction using a so-called peristaltic method of offsetting timings of deformation of the diaphragms (valve bodies) at predetermined intervals and controlling the opening and closing of the valves. Types and operation manners of the valves arranged in the flow path may be the same as each other or may be different from each other.

Further, as another example, by repeating the opening and closing of the single valve in a unit time, waves can be generated from the fluid in the flow path, and it is possible to allow the fluid to flow in a predetermined direction.

<<Summary of Embodiments of Fluidic Device Manufacturing Method>>

(1) A fluidic device manufacturing method includes: a first step of preparing a thinned elastomer sheet and a first resin substrate in which a concave microscopic groove capable of functioning as a flow path is formed on at least one surface; a second step of overlapping the first resin substrate and the elastomer sheet; and a third step of obtaining a substrate bond body by thermocompression bonding of the first resin substrate and the elastomer sheet.

(2) A fluidic device manufacturing method includes: a first step of overlapping a first resin substrate and an elastomer sheet; a second step of bonding the first resin substrate and the elastomer sheet according to thermocompression bonding, and a third step of, by overlapping and bonding the elastomer sheet and the second resin substrate according to thermocompression bonding, obtaining a substrate bond body of the first resin substrate/the elastomer sheet/the second resin substrate that are bonded in this order, wherein a microscopic structure that is recessed toward the inside of the substrate is formed in advance on a bond surface of at least one of the first resin substrate and the second resin substrate, and at least part of the microscopic structure is a groove capable of functioning as a flow path.

(3) A fluidic device is manufactured by the manufacturing method of (1) or (2) described above, the fluidic device includes: a resin substrate having a substrate surface and a plurality of flow paths formed on the substrate surface; an elastomer sheet that is bonded to at least part of the substrate surface and is arranged so as to cover the plurality of flow paths; and a valve structure in which the elastomer sheet functions as the diaphragm D of the valve in the flow path, wherein the Vicat softening temperature of the elastomer sheet is smaller than the Vicat softening temperature of the resin substrate.

According to the fluidic device manufacturing method of (1) and (2) described above, it is possible to form the layers (form a layered body) of a microfluidic device (micro-total analysis) including a valve and formed of a cartridge having a three-layer structure of the resin substrate/the elastomer sheet/the resin substrate.

According to the fluidic device manufacturing method of (1) described above, it is possible to reliably bond the first resin substrate and the elastomer sheet, and a fluidic device including a substrate bond body having a microscopic flow path can be easily manufactured.

According to the fluidic device manufacturing method of (2) described above, it is possible to reliably bond the first resin substrate, the elastomer sheet, and the second resin substrate that constitute a three-layer structure, and a fluidic device including a substrate bond body having a flow path inside the three-layer structure can be easily formed.

In the fluidic device of (3) described above, the resin substrate and the elastomer sheet are sufficiently strongly bonded, and therefore, the reliability and durability when the valve is repeatedly driven are excellent.

<<Fluidic Device Manufacturing Method>>

Figure 15:
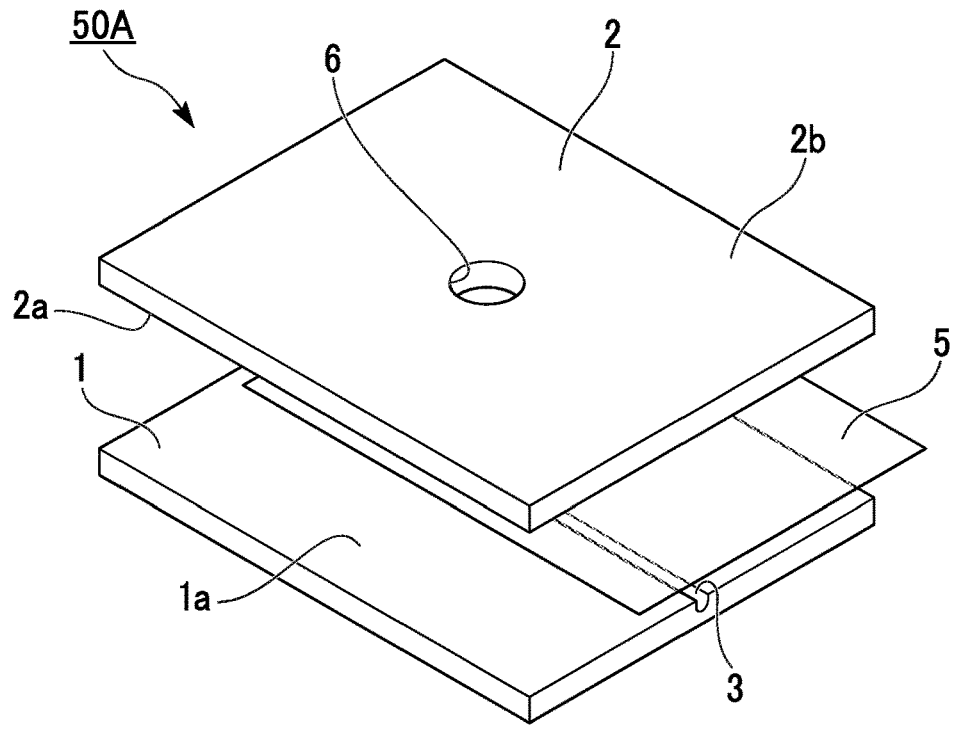
FIG. 15 is an exploded perspective view of the fluidic device and shows a way in which a first resin substrate, an elastomer sheet, and a second resin substrate that constitute the fluidic device are overlapped.

A first embodiment of a fluidic device manufacturing method includes: a first step of preparing a thinned elastomer sheet 5 and a first resin substrate 1 in which a groove 3 as a microscopic structure such as a recess capable of functioning as a flow path is formed on at least one surface 1a; a second step of overlapping the first resin substrate 1 and the elastomer sheet 5; and a third step of obtaining a substrate bond body 50A by thermocompression bonding of the first resin substrate 1 and the elastomer sheet 5 (refer to FIG. 15).

The above-described first embodiment of the manufacturing method may be a manufacturing method of a fluidic device including a valve that adjusts a fluid flow in a flow path 3. According to the above-described first embodiment of the manufacturing method, the above-described fluidic devices of the first to sixth embodiments can be manufactured. Hereinafter, as an example of the manufacturing method of the substrate bond body 50A, the manufacturing method of the fluidic device 10 is described.

In the first step of the first embodiment, the first resin substrate 1 (first substrate 1) in which the groove 3 having a depth h1 capable of functioning as the flow path 3 is formed on at least one surface 1a, and the protrusion part 4 is formed such that the depth of the flow path 3 at part of the bottom surface of the groove 3 is h3 that is shallower than h1; the second resin substrate 2 (second substrate 2) in which the base structure 6 that constitutes the valve is formed on the second surface 2a; and the elastomer sheet 5 that is thinned to be thinner than the first resin substrate 1 and the second resin substrate 2 are prepared.

In the second step of the first embodiment, the first resin substrate 1, the elastomer sheet 5, and the second resin substrate 2 are overlapped such that the elastomer sheet 5 is sandwiched between the first surface 1a of the first resin substrate 1 and the second surface 2a of the second resin substrate 2 and such that the protrusion part 4 faces the base structure 6. When seen in the thickness direction of the overlapped first resin substrate 1 and second resin substrate 2, the protrusion part 4 and the base structure 6 are overlapped with each other.

When overlapping the members, an alignment fiducial part (alignment mark) may be provided at any one or more members of the first resin substrate 1, the second resin substrate 2, and the elastomer sheet 5. In this case, when seen in the thickness direction of the overlapped first resin substrate 1 and second resin substrate 2 with reference to the alignment fiducial part, the first resin substrate 1, the elastomer sheet 5, and the second resin substrate 2 are overlapped such that the protrusion part 4 and the base structure 6 are overlapped. Examples of the alignment fiducial part include orthogonally crossed two lines and a mark. The base structure 6 of the valve may be used as the alignment fiducial part. As an example, when the orthogonally crossed two lines are provided on the first resin substrate 1 and the second resin substrate 2, alignment can be achieved by aligning the elastomer sheet 5 to the orthogonally crossed two lines.

In the third step of the first embodiment, the substrate bond body 50A is obtained by thermocompression bonding of the first resin substrate 1, the elastomer sheet 5, and the second resin substrate 2.

The heat and pressure in the thermocompression bonding is set in a range where the elastomer sheet 5 and the protrusion part 4 formed at a predetermined position of the bottom surface of the groove 3 provided on the first surface 1a of the first resin substrate 1 are not bonded to each other. For example, the heating is performed in atmospheric pressure and at a temperature higher than a room temperature.

In the above third step, as shown in FIG. 2 to FIG. 7, the elastomer sheet 5 and the second resin substrate 2 are fixed to each other at least at the first fixation part B1 and the second fixation part B2 to bridge the base structure 6.

A resin material for which the thermocompression bonding is applicable can be applied to a material that constitutes the first resin substrate 1 and the second resin substrate 2. Examples of the resin material include polycarbonate (PC), methacrylate styrene, polymethylmethacrylate resin (PMMA), and cycloolefin polymer (COP). The method of forming the groove 3 that constitutes a predetermined route on the first surface 1a of the first resin substrate 1, the method of forming the protrusion part 4 on the bottom surface of the groove 3, and the method of forming the base structure 6 of the valve on the second surface 2a of the second resin substrate 2 are not particularly limited, and microfabrication techniques such as molding, photolithography, and nanoimprint can be applied to the methods.

The second step and the third step in the manufacturing method of the first embodiment may include: a sub step of overlapping the first resin substrate 1 and the elastomer sheet 5; a sub step of bonding the first resin substrate 1 and the elastomer sheet 5 according to thermocompression bonding; and a sub step of, by overlapping and bonding the elastomer sheet 5 and the second resin substrate 2 according to thermocompression bonding, obtaining a substrate bond body 50 of the first resin substrate 1/the elastomer sheet 5/the second resin substrate 2 that are bonded in this order.

The groove 3 as a microscopic structure that is recessed toward the inside of the substrate is formed in advance on at least one of bond surfaces 1a, 2a of the first resin substrate 1 and the second resin substrate 2, and at least part of the microscopic structure 3 is a groove 3 capable of functioning as a flow path.

The elastomer sheet 5 bonded to the first surface 1a of the first resin substrate 1 according to thermocompression bonding (bonding according to heating and pressurization) is bonded to the first surface 1a of the first resin substrate 1. That is, the first surface 1a of the first resin substrate 1 is covered by the elastomer sheet 5.

The ceiling part (cap part) of the groove 3 (U-shaped groove) formed on the first surface 1a of the first resin substrate 1 is formed of the elastomer sheet 5. The area of the elastomer sheet 5 is equalized to the area of the first surface 1a of the first resin substrate 1, and therefore, the groove 3 that is sealed by the elastomer sheet 5 forms a flow path 3 that is closed other than an inflow port and an outflow port formed on the side surface of the first resin substrate 1.

The width of the groove 3 formed on the first surface 1a of the first resin substrate 1 is not particularly limited and can be appropriately set depending on the application. Examples of the width of the groove 3 include about 100 μm to 1000 μm. The depth h1 of the groove 3 formed on the first surface 1a of the first resin substrate 1 is not particularly limited and can be appropriately set depending on the application. Examples of the depth h1 of the groove 3 include about 100 μm to 1000 μm.

The number of grooves 3 formed on the first surface 1a of the first resin substrate 1 is not particularly limited and may be one. Alternatively, the number of grooves 3 may be two or more.

The route (shape) of the groove 3 formed on the first surface 1a of the first resin substrate 1 is not particularly limited, and shapes capable of forming straight, bent, and curved flow paths and the like may be appropriately combined.

The method of thermocompression bonding of the first resin substrate 1 and the elastomer sheet 5 is not particularly limited as long as the method does not cause a disadvantage that the elastomer sheet 5 is significantly deformed or shrunk due to the heating and pressurization or the like. As an example, first, the first resin substrate 1 and the elastomer sheet 5 are arranged at a predetermined relative position and are overlapped with each other, and a state is made in which the first resin substrate 1 and the elastomer sheet 5 are sandwiched while being pressured by a pressure addition plate. Next, by entirely and equally heating at least one of the first resin substrate 1 and the elastomer sheet 5 via the pressure addition plate, a substrate bond body in which the first resin substrate 1 and the elastomer sheet 5 are bonded to each other can be obtained. According to the above-described heating and pressurization method, the diaphragm D of the elastomer sheet 5 and the protrusion part 4 provided on the groove 3 at a position facing the diaphragm D are not bonded to each other, and it is possible to prevent the flow path 3 at the protrusion part 4 from closing to form a flow path 3 having an appropriate height and width.

In the substrate bond body, the first surface 1a of the first resin substrate 1 and the elastomer sheet 5 are bonded to each other. On the other hand, the inner wall surface and the bottom surface of the groove 3 which is a microscopic structure formed of a recess formed on the first surface 1a of the first resin substrate 1 and the protrusion part 4 provided on the bottom surface are neither in contact with the elastomer sheet 5 nor bonded to the elastomer sheet 5.

After the above-described thermocompression bonding, by continuing to add pressure until the first resin substrate 1 and the elastomer sheet 5 are cooled, it is possible to prevent the warpage or deformation of the substrate bond body in the cooling process.

In the thermocompression bonding of the first resin substrate 1 and the elastomer sheet 5, the melting point of the first resin substrate 1 can be higher than the Vicat softening temperature of the elastomer sheet 5, and the heating temperature during the thermocompression bonding of the first resin substrate 1 and the elastomer sheet 5 can be lower than the melting point of the first resin substrate 1 and be equal to or higher than the Vicat softening temperature of the elastomer sheet 5.

In the relationship between the melting point and the Vicat softening temperature, according to the thermocompression bonding at the above-described heating temperature, thermocompression bonding of the elastomer sheet 5 to the first resin substrate 1 is easily performed. Further, it is possible to prevent the shapes of the protrusion part 4 and the groove 3 formed on the first surface 1a of the first resin substrate 1 from being deformed due to the thermocompression bonding.

The difference between the melting point of the first resin substrate 1 and the Vicat softening temperature of the elastomer sheet 5 can be 10° C. or more.

When the temperature difference is in the above-described range, in thermocompression bonding, it is possible to soften the elastomer sheet 5 faster than the first resin substrate 1, and therefore, thermocompression bonding of the elastomer sheet 5 to the first resin substrate 1 can be further easily performed. Further, it is possible to further reliably prevent the shape of the groove 3 formed on the first surface 1a of the first resin substrate 1 from being deformed due to the thermocompression bonding.

In the step of the thermocompression bonding of the first resin substrate 1 and the elastomer sheet 5, the Vicat softening temperature of the first resin substrate 1 can be higher than the Vicat softening temperature of the elastomer sheet 5, and the heating temperature during the thermocompression bonding of the first resin substrate 1 and the elastomer sheet 5 can be lower than the Vicat softening temperature of the first resin substrate 1 and be equal to or higher than the Vicat softening temperature of the elastomer sheet 5.

In the relationship between the Vicat softening temperatures, according to the thermocompression bonding at the above-described heating temperature, thermocompression bonding of the elastomer sheet 5 to the first resin substrate 1 is easily performed. Further, it is possible to further reliably prevent the shapes of the protrusion part 4 and the groove 3 formed on the first surface 1a of the first resin substrate 1 from being deformed due to the thermocompression bonding.

The difference between the Vicat softening temperature of the first resin substrate 1 and the Vicat softening temperature of the elastomer sheet 5 can be 5° C. or more.

When the temperature difference is in the above-described range, in thermocompression bonding, it is possible to soften the elastomer sheet 5 faster than the first resin substrate 1, and therefore, thermocompression bonding of the elastomer sheet 5 to the first resin substrate 1 can be further easily performed. Further, it is possible to further reliably prevent the shape of the groove 3 formed on the first surface 1a of the first resin substrate 1 from being deformed due to the thermocompression bonding.

In the step of the thermocompression bonding of the first resin substrate 1 and the elastomer sheet 5, the thickness of the first resin substrate 1 can be thicker than the thickness of the elastomer sheet 5.

In the relationship between the thicknesses, according to the thermocompression bonding at the above-described heating temperature, thermocompression bonding of the elastomer sheet 5 to the first resin substrate 1 is easily performed. Further, it is possible to prevent the shapes of the protrusion part 4 and the groove 3 formed on the first surface 1a of the first resin substrate 1 from being deformed due to the thermocompression bonding.

The thickness of the first resin substrate 1 is not particularly limited and can be appropriately set depending on the application of the fluidic device. Examples of the thickness of the first resin substrate 1 include a thickness of about 2 mm to 5 mm.

When the thickness is in the above-described range, it is possible to prevent the deformation of the first resin substrate 1, the deformation of the groove 3, and the deformation of the protrusion part 4 due to the thermocompression bonding. The thickness of the first resin substrate 1 can be made uniform over the entire substrate.

The thickness of the elastomer sheet 5 is not particularly limited and can be appropriately set depending on the application of the fluidic device. Examples of the thickness of the elastomer sheet 5 include a thickness of about 300 µm to 800 µm.

When the thickness is in the above-described range, it is possible to prevent the deformation and shrinkage of the elastomer sheet 5 due to the thermocompression bonding. The thickness of the elastomer sheet 5 can be made uniform over the entire sheet.

The base structure 6 of the valve, which is a microscopic structure that is recessed toward the inside of the substrate, is formed in advance on the second surface 2a (lower surface 2a) of the second resin substrate 2. The base structure 6 in the present embodiment is a through-hole 6 that opens at the lower surface 2a and the upper surface 2b of the second resin substrate 2. It is possible to allow air to flow through the through-hole 6.

The second resin substrate 2 is bonded via the elastomer sheet 5 to the substrate bond body including the elastomer sheet 5 bonded to the first surface 1a of the first resin substrate 1 according to the thermocompression bonding to thereby obtain the fluidic device 10 as an example of the substrate bond body 50A.

In the fluidic device 10 bonded such that the through-hole 6 is positioned immediately above the groove 3 to interpose the elastomer sheet 5, by delivering air to the through-hole 6 and adding pressure, it is possible to cause the elastomer sheet 5 to expand in the direction of the groove 3, and the groove 3 can be closed. Further, when the pressure according to air is released, the expansion of the elastomer sheet 5 returns to the original position by an elastic force and disappears. That is, the elastomer sheet 5 functions as the diaphragm D of the valve structure, and therefore, it is possible to control the flow of the flow path formed of the groove 3.

From the viewpoint that the elastomer sheet 5 sufficiently functions as the diaphragm D of the valve structure, the thickness of the elastomer sheet 5 is, for example, 300 µm to 800 µm.

From the viewpoint that the elastomer sheet 5 sufficiently functions as the diaphragm D of the valve structure, the repulsion elasticity of the elastomer sheet 5 is, for example, 50 to 60%, and the tension strength is 3 to 15 MPa. Here, the repulsion elasticity is a value obtained according to a measurement method that is compliant to JIS K 6255, and the tension strength is a value obtained according to a measurement method that is compliant to JIS K 6251.

The areas of the first resin substrate 1, the elastomer sheet 5, and the second resin substrate 2 are equal to each other, and therefore, the fluidic device 10 in which the first resin substrate 1, the elastomer sheet 5, and the second resin substrate 2 are laminated and bonded to each other is formed as a fluidic device having a card shape (rectangle) in which the end parts of the substrates are aligned in each side.

The diameter (hole diameter) of the through-hole 6 formed on the second resin substrate 2 is not particularly limited and can be appropriately set depending on the application. Examples of the diameter of the through-hole 6 include about 300 µm to 1000 µm.

The length in the longitudinal direction of the through-hole 6 formed on the second resin substrate 2 is not particularly limited and can be appropriately set depending on the application. The axis line (line corresponding to the center axis) of the through-hole 6 may be parallel to the thickness direction of the second resin substrate 2 or may be non-parallel to the thickness direction of the second resin substrate 2. When the axis line of the through-hole 6 is parallel to the thickness direction of the second resin substrate 2, the length of the through-hole 6 is the same as the thickness of the second resin substrate 2. When the axis line of the through-hole 6 is non-parallel to the thickness direction of the second resin substrate 2, the length of the through-hole 6 is longer than the thickness of the second resin substrate 2. Examples of the length of the through-hole 6 include about 300 µm to 1500 µm.

The number of through-holes 6 formed on the second resin substrate 2 is not particularly limited and may be one. Alternatively, the number of through-holes 6 may be two or more. When forming a plurality of through-holes 6, the opening part of each through-hole 6 can be positioned immediately above the groove 3. According to the arrangement, each through-hole 6 can function as part of the valve structure in the flow path formed of the groove 3.

The route (shape) of the through-hole 6 formed on the second resin substrate 2 is not particularly limited, and shapes capable of forming straight, bent, and curved flow paths and the like may be appropriately combined.

The method of thermocompression bonding of the second resin substrate 2 and the elastomer sheet 5 bonded to the first resin substrate 1 that constitutes the substrate bond body is not particularly limited as long as the method does not cause a disadvantage that the resin substrates 1, 2 and the elastomer sheet 5 are significantly deformed or shrunk due to the heating and pressurization or the like. As an example, first, the second resin substrate 2 and the substrate bond body are arranged at a predetermined relative position and are overlapped with each other, and a state is made in which the first surface 1a of the first resin substrate 1 and the second surface 2a of the second resin substrate 2 interposes the elastomer sheet 5 while being pressed by a pressure addition plate. Next, by entirely and equally heating at least one of the first resin substrate 1 and the second resin substrate 2 via the pressure addition plate, the fluidic device 10 can be obtained as an example of the substrate bond body 50A in which the first resin substrate 1 and the second resin substrate 2 are bonded to each other via the elastomer sheet 5.

In the fluidic device 10, the second surface 2a of the second resin substrate 2 and the elastomer sheet 5 are bonded to each other. On the other hand, the inner side surface (inner wall surface) of the through-hole 6 which is a microscopic structure formed of a recess formed on the second surface 2a of the second resin substrate 2 is neither in contact with the elastomer sheet 5 nor bonded to the elastomer sheet 5.

After the above-described thermocompression bonding, by continuing to add pressure until the first resin substrate 1, the elastomer sheet 5, and the second resin substrate 2 are cooled, it is possible to prevent the warpage or deformation of the fluidic device 10 in the cooling process.

The melting point of the second resin substrate 2 can be higher than the Vicat softening temperature of the elastomer sheet 5, and the heating temperature during the thermocompression bonding can be lower than the melting point of the second resin substrate 2 and be equal to or higher than the Vicat softening temperature of the elastomer sheet 5.

In the relationship between the melting point and the Vicat softening temperature, according to the thermocompression bonding at the above-described heating temperature, thermocompression bonding of the elastomer sheet 5 to the second resin substrate 2 is easily performed. Further, it is possible to prevent the shape of the through-hole 6 formed on the second resin substrate 2 from being deformed due to the thermocompression bonding.

The difference between the melting point of the second resin substrate 2 and the Vicat softening temperature of the elastomer sheet 5 can be 10° C. or more. When the temperature difference is in the above-described range, in thermocompression bonding, it is possible to soften the elastomer sheet 5 faster than the second resin substrate 2, and therefore, thermocompression bonding of the elastomer sheet 5 to the second resin substrate 2 can be further easily performed. Further, it is possible to further reliably prevent the shape of the through-hole 6 formed on the second resin substrate 2 from being deformed due to the thermocompression bonding.

In the step of the thermocompression bonding of the second resin substrate 2 and the elastomer sheet 5, the Vicat softening temperature of the second resin substrate 2 can be higher than the Vicat softening temperature of the elastomer sheet 5, and the heating temperature during the thermocompression bonding can be lower than the Vicat softening temperature of the second resin substrate 2 and be equal to or higher than the Vicat softening temperature of the elastomer sheet 5.

In the relationship between the Vicat softening temperatures, according to the thermocompression bonding at the above-described heating temperature, thermocompression bonding of the elastomer sheet 5 to the second resin substrate 2 is easily performed. Further, it is possible to further reliably prevent the shape of the through-hole 6 formed on the second resin substrate 2 from being deformed due to the thermocompression bonding.

The difference between the Vicat softening temperature of the second resin substrate 2 and the Vicat softening temperature of the elastomer sheet 5 can be 5° C. or more.

When the temperature difference is in the above-described range, in thermocompression bonding, it is possible to soften the elastomer sheet 5 faster than the second resin substrate 2, and therefore, thermocompression bonding of the elastomer sheet 5 to the second resin substrate 2 can be further easily performed. Further, it is possible to further reliably prevent the shape of the through-hole 6 formed on the second resin substrate 2 from being deformed due to the thermocompression bonding.

In the step of the thermocompression bonding of the second resin substrate 2 and the elastomer sheet 5, the thickness of the second resin substrate 2 can be thicker than the thickness of the elastomer sheet 5.

In the relationship between the thicknesses, according to the thermocompression bonding at the above-described heating temperature, thermocompression bonding of the elastomer sheet 5 to the second resin substrate 2 is easily performed. Further, it is possible to prevent the shape of the through-hole 6 formed on the second resin substrate 2 from being deformed due to the thermocompression bonding.

The thickness of the second resin substrate 2 is not particularly limited and can be appropriately set depending on the application of the fluidic device. Examples of the thickness of the second resin substrate 2 include a thickness of about 0.5 mm to 1 mm.

When the thickness is in the above-described range, it is possible to prevent the deformation of the second resin substrate 2 and the shape of the through-hole 6 due to the thermocompression bonding. The thickness of the second resin substrate 2 can be made uniform over the entire substrate.

Figure 16:
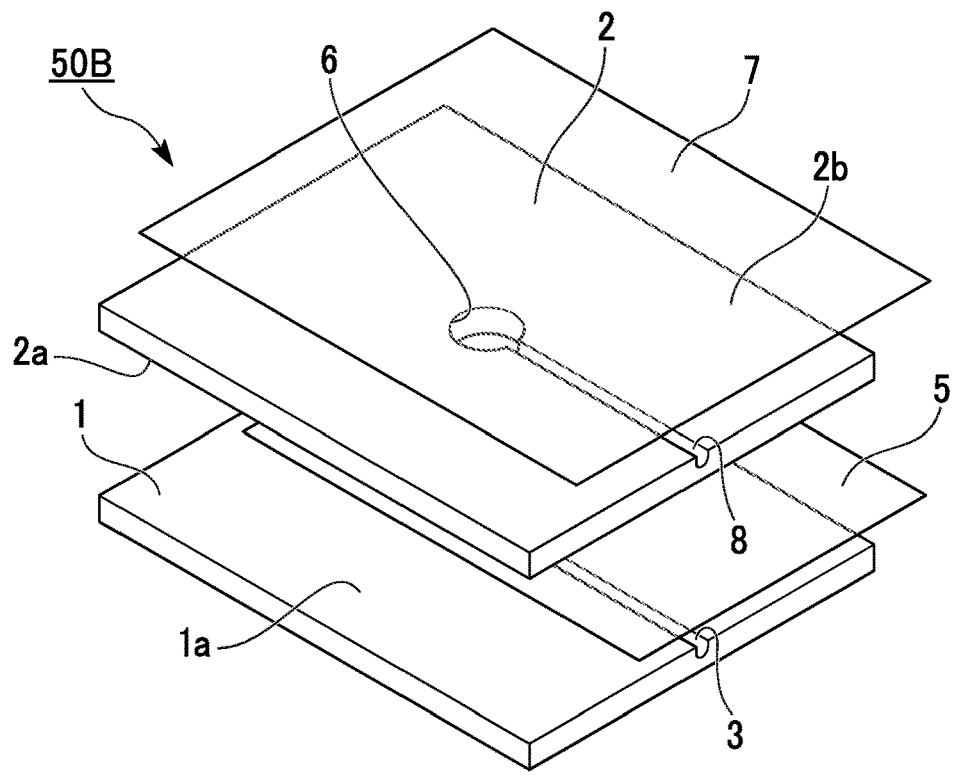
FIG. 16 is an exploded perspective view of the fluidic device having a resin film and shows a way in which the first resin substrate, the elastomer sheet, the second resin substrate, and the resin film that constitute the fluidic device are overlapped.

As shown in FIG. 16, a groove 8 as an example of the microscopic structure that is recessed toward the inside of the substrate may be formed on an upper surface 2b (outer substrate surface) of the second resin substrate 2. In the example of the fluidic device as a substrate bond body 50B of FIG. 16, a first end part of the groove 8 is positioned on the side surface of the second resin substrate 2, and a second end part is positioned on the side surface (edge) of the through-hole 6. The groove 8 is capable of functioning as a flow path.

In the fluidic device manufacturing method, by further overlapping a resin film 7 on the outer substrate surface (upper surface 2b) of the second resin substrate 2 that constitutes the substrate bond body 50A and bonding the resin film 7 and the second resin substrate 2 according to thermocompression bonding, the groove 8 as an example of the microscopic structure that is recessed toward the inside of the substrate formed in advance on the outer substrate surface can be covered by the resin film 7.

When the resin film 7 is bonded to the upper surface 2b of the second resin substrate 2 according to thermocompression bonding, the upper surface 2b of the second resin substrate 2 is covered by the resin film 7. In this case, the ceiling part (cap part) of the groove 8 (U-shaped groove) formed on the second surface 2b of the second resin substrate 2 is formed of the resin film 7. The area of the resin film 7 is equalized to the area of the upper surface 2b of the second resin substrate 2, and therefore, the groove 8 that is sealed by the resin film 7 forms a flow path 3 that is closed other than an inflow port formed on the side surface of the second resin substrate 2 and an outflow port formed on the side surface of the through-hole 6.

The width of the groove 8 formed on the upper surface 2b of the second resin substrate 2 is not particularly limited and can be appropriately set depending on the application. Examples of the width of the groove 8 include about 100 μm to 1000 μm.

The depth of the groove 8 formed on the upper surface 2b of the second resin substrate 2 is not particularly limited and can be appropriately set depending on the application. Examples of the depth of the groove 8 include about 50 μm to 500 μm.

The number of grooves 8 formed on the upper surface 2b of the second resin substrate 2 is not particularly limited and may be one. Alternatively, the number of grooves 8 may be two or more.

The route (shape) of the groove 8 formed on the upper surface 2b of the second resin substrate 2 is not particularly limited, and shapes capable of forming straight, bent, and curved flow paths and the like may be appropriately combined.

The method of thermocompression bonding of the resin film 7 and the second resin substrate 2 that constitutes the substrate bond body 50B is not particularly limited as long as the method does not cause a disadvantage that the resin substrates 1, 2, the elastomer sheet 5, and the resin film 7 are significantly deformed or shrunk due to the heating and pressurization or the like. As an example, first, the second resin substrate 2 and the resin film 7 are arranged at a predetermined relative position and are overlapped with each other, and a state is made in which the above-described substrate bond body 50A and the resin film 7 are sandwiched while being pressured by a pressure addition plate. Next, by entirely and equally heating at least one of the substrate bond body 50A and the resin film 7 via the pressure addition plate, it is possible to obtain the substrate bond body 50B in which the resin film 7 and the upper surface 2b of the second resin substrate 2 that constitutes the substrate bond body 50A are bonded to each other.

In the substrate bond body 50B, the upper surface 2b of the second resin substrate 2 and the resin film 7 are bonded to each other. On the other hand, the inner wall surface and the bottom surface of the groove 8 and the inner wall surface (inner side surface) of the through-hole 6 which is the microscopic structure formed of a recess formed on the upper surface 2b of the second resin substrate 2 are neither in contact with the resin film 7 nor bonded to the resin film 7.

After the above-described thermocompression bonding, by continuing to add pressure until the resin substrates 1, 2, the elastomer sheet 5, and the resin film 7 are cooled, it is possible to prevent the warpage or deformation of the substrate bond body 50B in the cooling process.

In the step of thermocompression bonding of the resin film 7 and the second resin substrate 2 that constitutes the substrate bond body 50B, the melting point of the second resin substrate 2 can be higher than the Vicat softening temperature of the resin film 7, and the heating temperature during the thermocompression bonding can be lower than the melting point of the second resin substrate 2 and be equal to or higher than the Vicat softening temperature of the resin film 7.

In the relationship between the melting point and the Vicat softening temperature, according to the thermocompression bonding at the above-described heating temperature, thermocompression bonding of the resin film 7 to the second resin substrate 2 is easily performed. Further, it is possible to prevent the shapes of the groove 8 and the through-hole 6 formed on the second resin substrate 2 from being deformed due to the thermocompression bonding.

The difference between the melting point of the second resin substrate 2 and the Vicat softening temperature of the resin film 7 can be 10° C. or more.

When the temperature difference is in the above-described range, in thermocompression bonding, it is possible to soften the resin film 7 faster than the second resin substrate 2, and therefore, thermocompression bonding of the resin film 7 to the second resin substrate 2 can be further easily performed. Further, it is possible to further reliably prevent the shapes of the groove 8 and the through-hole 6 formed on the second resin substrate 2 from being deformed due to the thermocompression bonding.

In the step of the thermocompression bonding of the resin film 7 and the second resin substrate 2 that constitutes the substrate bond body 50B, the thickness of the second resin substrate 2 can be thicker than the thickness of the resin film 7.

In the relationship between the thicknesses, according to the thermocompression bonding at the above-described heating temperature, thermocompression bonding of the resin film 7 to the second resin substrate 2 is easily performed. Further, it is possible to prevent the shapes of the groove 8 and the through-hole 6 formed on the second resin substrate 2 from being deformed due to the thermocompression bonding.

The thickness of the resin film 7 is not particularly limited and can be appropriately set depending on the application of the fluidic device. Examples of the thickness of the resin film 7 include a thickness of about 100 μm to 300 μm.

When the thickness is in the above-described range, it is possible to prevent the deformation and shrinkage of the resin film 7 due to the thermocompression bonding.

The thickness of the resin film 7 can be made uniform over the entire film.

Before the thermocompression bonding of the resin film 7 and the second resin substrate 2 that constitutes the substrate bond body 50B, for example, a surface treatment is applied in advance on at least one of bond surfaces of the second resin substrate 2 and the resin film 7.

A known method capable of improving the bond property or adhesion property of the bond surface is applicable to the surface treatment, and examples of the surface treatment include property modification or purification of the bond surface according to UV irradiation, ozone exposure, oxygen plasma exposure, or the like.

It is possible to measure the "Vicat softening temperature" using a method that is compliant to JIS. K. 7206.

It is possible to measure the "melting point" using a method that is compliant to JIS. K. 0064.

It is possible to measure the "thickness" of the first resin substrate 1, the elastomer sheet 5, the second resin substrate 2, and the resin film 7 using a method that is compliant to ISO 3599.

In the fluidic device obtained by the first embodiment of the manufacturing method described above, the microscopic structure formed on the substrate surface that constitutes the bond surface of the substrate bond body is utilized as a flow path, a fluid flows in the flow path, and the elastomer sheet bonded to the bond surface of the substrate according to thermocompression bonding is capable of functioning as the diaphragm D of the valve that controls the flow of the fluid. Since the flow path is at a microscale, it is important to design the size precisely and to manufacture the fluidic device at the designed size. Further, since not only the flow path but also the through-hole that constitutes the valve structure and the groove for delivering air to the through-hole are similarly at a microscale, it is important to design the size precisely and to manufacture the fluidic device at the designed size. Further, in order for the elastomer sheet bonded to the substrate to function as the diaphragm D of the valve, it is required that, in a local position (microscopic area) in the microscopic structure, the elastomer sheet be deformed by external air pressure and return to the original position by an elastic force of the elastomer sheet when the air pressure is released. In such a valve driving, it is required that the substrate and the elastomer sheet be sufficiently bonded (adhere) to prevent the elastomer sheet from removing from the substrate due to the valve driving.

In the first embodiment of the manufacturing method described above, the substrate and the elastomer sheet are bonded according to thermocompression bonding. If the object is merely to strongly bond the substrate and the elastomer sheet, by performing thermocompression bonding at as high a temperature as possible in a range where the substrate is not significantly deformed, the elastomer sheet is melted to perform the thermocompression bonding without considering the deformation of the elastomer sheet.

However, according to such a method, a problem may easily occur in which the melted elastomer sheet flows into the microscopic structure that is recessed toward the inside of the substrate surface and fills the microscopic structure. Therefore, in the manufacturing method according to the embodiment of the present invention, as described above, according to the temperature property and thickness of each of the first resin substrate, the elastomer sheet, the second resin substrate, and the resin film, the above-described problem is avoided, and a necessary and sufficient bond force for tolerating the repeated valve driving is realized.

In the first embodiment of the manufacturing method described above, the substrate and the elastomer sheet are bonded according to thermocompression bonding, and therefore, an adhesive agent that may be eluted to the liquid flowing in the flow path and a clip that is physically large are unnecessary. Therefore, the fluidic device as the substrate bond body obtained by the first embodiment of the manufacturing method described above is advantageous for applications in which the elution of an adhesive agent may be a problem, such as an inspection chip application, a test chip application, and the like used in a biotechnology, medicine, medical, or chemical field and the like. In addition, further size reduction is required for the inspection chip, test chip, and the like, and therefore, it is extremely advantageous that a clip that is physically large is unnecessary.

Next, as a modified example of the substrate bond body 50B described above, a fluidic device as a substrate bond body 50C is described. As shown in the exploded perspective view of FIG. 17, the substrate bond body 50C includes: a first resin substrate 1 having a first surface 1a and a plurality of flow paths 3 formed on the first surface 1a; a single elastomer sheet 5 that is bonded to at least part of the first surface 1a and is arranged so as to cover the plurality of flow paths 3; and a valve structure in which the single elastomer sheet 5 functions as the diaphragm D of the plurality of valves. The Vicat softening temperature of the elastomer sheet 5 that constitutes the substrate bond body 50C is smaller than the Vicat softening temperature of the first resin substrate 1.

Figure 17:
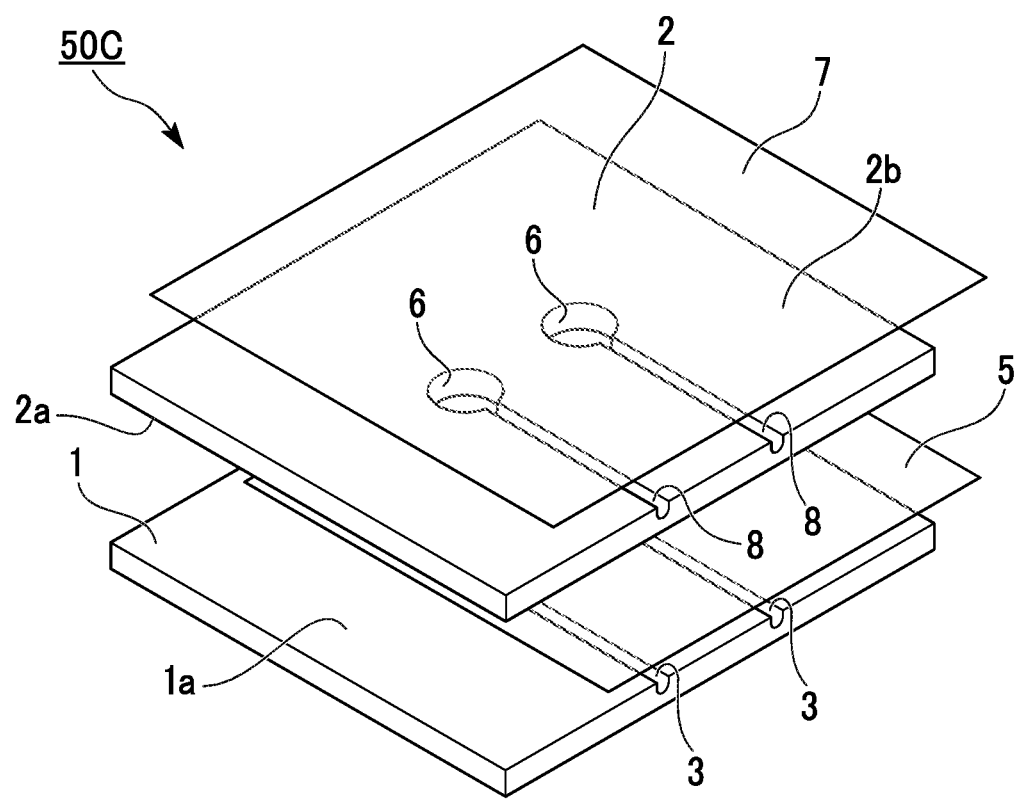
FIG. 17 is an exploded perspective view of the fluidic device having the resin film and shows a way in which the first resin substrate, the elastomer sheet, the second resin substrate, and the resin film that constitute the fluidic device are overlapped.

The description of members that constitute the substrate bond body 50C shown in the exploded perspective view of FIG. 17 is the same as the description of members that constitute the substrate bond bodies 50A, 50B described above and therefore is omitted. The same reference numeral is given to a member that is common between the substrate bond body 50C and the substrate bond bodies 50A, 50B. The exploded perspective view of the fluidic device as the substrate bond body 50C shown in FIG. 17 is a view showing only a main part and does not show the entire fluidic device. Similarly, the view of the fluidic device shown in FIG. 1 to FIG. 16 is also a view showing only a main part of the fluidic device and does not show the entire fluidic device.

The flow path 3 is formed of the groove 3 which is a microscopic structure formed on the first surface 1a of the first resin substrate 1. In the present embodiment, the number of grooves 3 formed on the first surface 1a of the first resin substrate 1 is two or more.

Examples of the preferable elastomer that constitutes the elastomer sheet 5 include a polystyrene-system elastomer and a silicone resin-system elastomer. Here, the term "system" means that the content of the resin to the total mass of the elastomer is 50 mass % or more.

The valve structure included in the substrate bond body 50C includes at least: a plurality of grooves 3 formed on the first surface 1a of the first resin substrate 1; a single elastomer sheet 5 that constitutes a ceiling part of the plurality of grooves 3 and is bonded to the first surface 1a; a second resin substrate 2 that is bonded to the first surface 1a of the first resin substrate 1 via the elastomer sheet 5; and a plurality of through-holes 6 penetrating through the second resin substrate 2 and arranged such that one of the plurality of through-holes 6 is positioned immediately above each of the plurality of the grooves 3. Each one of the plurality of through-holes 6 is formed of a plurality of inner side surfaces formed on the second resin substrate 2.

The substrate bond body 50C further includes: a plurality of grooves 8 formed on the upper surface 2b of the second resin substrate 2 and each connected to one of the through-holes 6; and a resin film 7 bonded to the upper surface 2b of the second resin substrate 2.

When delivering air from the opening part of the groove 8 that opens at the side surface of the second resin substrate 2, the air passes through the through-hole 6 and presses down part of the elastomer sheet 5 bonded to the lower surface 2a (second surface 2a) of the second resin substrate 2 toward the inside of the groove 3, and the flow of the fluid in the flow path formed of the groove 3 is blocked. Then, when the delivery of the air is stopped, the air pressure is released, and the part of the elastomer sheet 5 that has fallen inside the groove 3 returns to the original position by an elastic force to restart the flow of the liquid in the flow path.

The valve driving system described above is a so-called normally open system (system in which a flow path is open in a state where air pressure is absent). However, by adopting the valve structure as described in FIG. 1 of "PMMA/PDMS Valves and Pumps for Disposable Microfluidics." Lab Chip. 2009 Nov. 7; 9 (21): 3088-94, Zhang W et al., the valve driving system described above can also be a so-called normally closed system (system in which a flow path is closed in a state where air pressure is absent).

The fluidic device as the substrate bond body 50C is manufactured by the above-described manufacturing method, and therefore, according to thermocompression bonding, the first resin substrate 1, the elastomer sheet 5, the second resin substrate 2, and the resin film 7 are sufficiently strongly bonded to each other.

As a result, a problem does not easily occur in which the liquid that flows through the flow path 3 may leak into a gap formed when the bonding between the first resin substrate 1 and the elastomer sheet 5 are removed or the liquid that flows through the first flow path 3 and the liquid that flows through the adjacent second flow path 3 may be mixed with each other. Similarly, a problem does not easily occur in which the air that is delivered to the flow path 8 formed of the groove 8 may leak into a gap formed when the bonding between the second resin substrate 2 and the resin film 7 are removed or the air that flows through the first flow path 8 may flow into the adjacent second flow path 8.

The single elastomer sheet 5 is bonded to the first surface 1a of the first resin substrate 1 to bridge the plurality of grooves 3. Here, if an individual elastomer sheet is bonded to each groove 3, due to the convenience of manufacturing, a region occurs in which part of the first surface 1a of the first resin substrate 1 is not bonded by the elastomer sheet. In this case, the bond area is reduced. On the other hand, in the substrate bond body 50C, since the single elastomer sheet 5 is bonded to the first surface 1a of the first resin substrate 1 over a broad range, the bond area of the single elastomer sheet 5 and the first surface 1a of the first resin substrate 1 is broadened, and strong bonding is realized.

Similarly, the single resin film 7 is bonded to the upper surface 2b of the second resin substrate 2 to bridge the grooves 8 and the through-holes 6. Here, if an individual resin film is bonded to each groove 8, due to the convenience of manufacturing, a region occurs in which part of the upper surface 2b of the second resin substrate 2 is not bonded by the resin film. In this case, the bond area is reduced. On the other hand, in the substrate bond body 50C, since the single resin film 7 is bonded to the upper surface 2b of the second resin substrate 2 over a broad range, the bond area of the single resin film 7 and the upper surface 2b of the second resin substrate 2 is broadened, and strong bonding is realized.

According to the fluidic device of the embodiment described above, it is possible to easily control a fluid flow in a flow path.

According to the fluid control method of the embodiment described above, bubbles mixed when a liquid is introduced to the flow path can be separated from the liquid at the valve structure provided in the flow path and including the protrusion part. As a result, it is possible to prevent unnecessary bubbles from arriving at the delivery destination of the liquid.

According to the testing method utilizing the testing device of the embodiment described above, it is possible to easily detect an inspection target material in a liquid sample.

According to the fluidic device manufacturing method of the embodiment described above, it is possible to strongly bond the first substrate and the second substrate without damaging the flow path and the valve structure included in the fluidic device.

What is claimed is:

1. A micro fluidic device comprising:
a first substrate having a groove and a protrusion formed in the groove;
a second substrate being at a position facing the groove and the protrusion of the first substrate, the second substrate and the groove and the protrusion of the first substrate constituting a fluid flow path; and
a sheet having a diaphragm part and a fixation part, the diaphragm part being at a position facing the protrusion of the first substrate, the diaphragm part and the protrusion being configured to constitute a valve of the fluid flow path for adjusting a fluid flow, and the fixation part of the sheet being sandwiched between the first substrate and the second substrate,
wherein
a length of the protrusion, as measured along a direction of the fluid flow path, of the first substrate is greater than a length of the diaphragm part, as measured along the direction of the fluid flow path, of the sheet.

2. The micro fluidic device according to claim 1, wherein the second substrate has an opening at a position facing the diaphragm part of the sheet, and
the length of the diaphragm part, as measured along a direction of the fluid flow path, is equal to or greater than a length of the opening, as measured along a direction of the fluid flow path.

3. The micro fluidic device according to claim 2, wherein the second substrate comprises a hole having the opening at the end of the hole.

4. The micro fluidic device according to claim 3, wherein the valve is in an open state when a pressure is not delivered or a reduced pressure is delivered through the hole to the diaphragm part thought the opening, and the valve is in a closed state when a pressure is deliver through the hole to the diaphragm part through the opening.

5. The micro fluidic device according to claim 4, wherein an upstream side of the protrusion in the fluid flow path is substantially perpendicular to the direction of the fluid flow path.

6. A fluid control method in a micro fluidic device, the micro fluidic device comprising:
   a first substrate having a groove and a protrusion formed in the groove;
   a second substrate being at a position facing the groove and the protrusion of the first substrate, the second substrate and the groove and the protrusion of the first substrate constituting a fluid flow path; and
   a sheet having a diaphragm part and a fixation part, the diaphragm part being at a position facing the protrusion of the first substrate, the diaphragm part and the protrusion being configured to constitute a valve of the fluid flow path for adjusting a fluid flow, and the fixation part of the sheet being sandwiched between the first substrate and the second substrate; wherein
   a length of the protrusion, as measured along a direction of the fluid flow path, of the first substrate is greater than a length of the diaphragm part, as measured along the direction of the fluid flow path, of the sheet, wherein the control method comprises:
   (a) by delivering a pressure to the diaphragm part, deforming the diaphragm part toward the protrusion so that the diaphragm part comes into contact with the protrusion, thereby the valve is in a closed state;
   (b) introducing a fluid to the flow path and delivering the fluid until a front end of the fluid arrives at the position of the protrusion;
   (c) by reducing the pressure to the diaphragm part, allowing the fluid to pass through the protrusion, thereby the valve is in an open state.

7. The fluid control method according to claim 6, wherein a deformation amount of the diaphragm part toward the protrusion is controlled by an amount of pressure to the diaphragm part.

8. The micro fluidic device according to claim 1, wherein the protrusion of the first substrate is not moveable.

9. The micro fluidic device according to claim 1, wherein the diaphragm part of the sheet is made of a flexible material, and the diaphragm part is deformable toward the protrusion of the first substrate.

10. The micro fluidic device according to claim 1, wherein a depth of the groove is greater than a height of the protrusion.

11. A micro fluidic device comprising:
    a first substrate having a groove and a protrusion in the groove, a depth of the groove is greater than a height of the protrusion;
    a second substrate being at a position facing the groove and the protrusion of the first substrate, the second substrate and the groove and the protrusion of the first substrate constituting a fluid flow path; and
    a sheet having a diaphragm part and a fixation part, the diaphragm part being at a position facing the protrusion of the first substrate, and the fixation part being sandwiched between the first substrate and the second substrate;
    wherein the second substrate has an opening at a position facing the protrusion of the first substrate to deliver a pressure to the diaphragm part, and the diaphragm part, the protrusion and the opening constitute a valve of the fluid flow path for adjusting a fluid flow.

12. The micro fluidic device according to claim 11, wherein the second substrate has a hole such that the pressure can be delivered through the hole to the diaphragm part via the opening.

13. The micro fluidic device according to claim 12, wherein
    the valve is in an open state when a pressure is not delivered or a reduced pressure is delivered through the hole to the diaphragm part thought the opening, and the valve is in a closed state when a pressure is delivered through the hole to the diaphragm part through the opening.

14. The micro fluidic device according to claim 11, wherein an upstream side of the protrusion in the fluid flow path is substantially perpendicular to the direction of the fluid flow path.

15. The micro fluidic device according to claim 11, wherein a length of the protrusion, as measured along a direction of the fluid flow path, of the first substrate is greater than a length of the diaphragm part, as measured along the direction of the fluid flow path, of the sheet.

16. The micro fluidic device according to claim 11, wherein a length of the diaphragm part, as measured along a direction of the fluid flow path, is equal to or greater than a length of the opening, as measured along a direction of the fluid flow path.

17. The micro fluidic device according to claim 11, wherein the protrusion of the first substrate is not moveable.

18. The micro fluidic device according to claim 11, wherein the diaphragm part of the sheet is made of a flexible material, and the diaphragm part is deformable toward the protrusion of the first substrate.

* * * * *